United States Patent
Faion-Molina et al.

(10) Patent No.: US 10,774,335 B2
(45) Date of Patent: Sep. 15, 2020

(54) METHOD FOR TRANSFORMING A PLANT CELL OR PLANT TISSUE USING AGROBACTERIUM, TRANSGENIC PLANT, TRANSGENIC CELL OR TRANSGENIC TISSUE, CULTURE MEDIUM AND USE OF A METHOD FOR TRANSFORMING A PLANT CELL OR TISSUE

(71) Applicant: CTC—Centro de Tecnologia Canavieira S.A., Piracicaba, Sao Paulo (BR)

(72) Inventors: Mayra Faion-Molina, Americana (BR); Paulo Cezar De Lucca, Campinas (BR)

(73) Assignee: CTC—Centro de Tecnologia Canavieira S.A., Piracicaba, Sao Paulo (BR)

( * ) Notice: Subject to any disclaimer, the term of this patent is extended or adjusted under 35 U.S.C. 154(b) by 0 days.

(21) Appl. No.: 15/514,377

(22) PCT Filed: Sep. 16, 2015

(86) PCT No.: PCT/BR2015/050154
§ 371 (c)(1),
(2) Date: Mar. 24, 2017

(87) PCT Pub. No.: WO2016/044909
PCT Pub. Date: Mar. 31, 2016

(65) Prior Publication Data
US 2017/0298371 A1    Oct. 19, 2017

(30) Foreign Application Priority Data
Sep. 26, 2014   (BR) ..................... BR1020140239308

(51) Int. Cl.
*A01H 4/00* (2006.01)
*C12N 15/82* (2006.01)

(52) U.S. Cl.
CPC ......... *C12N 15/8205* (2013.01); *A01H 4/008* (2013.01); *C12N 15/8201* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 5,380,831 A | 1/1995 | Adang et al. | |
| 5,436,391 A | 7/1995 | Fujimoto et al. | |
| 5,563,055 A | 10/1996 | Townsend et al. | |
| 5,591,616 A | 1/1997 | Hiei et al. | |
| 5,981,840 A | 11/1999 | Zhao et al. | |
| 6,323,396 B1 | 11/2001 | Dirks et al. | |
| 7,951,923 B2 | 5/2011 | Lukyanov et al. | |
| 2013/0055472 A1 | 2/2013 | Cho et al. | |

FOREIGN PATENT DOCUMENTS

| | | |
|---|---|---|
| CN | 101768604 A | 7/2010 |
| WO | WO 94/00977 A1 | 1/1994 |
| WO | WO 98/54961 A2 | 12/1998 |
| WO | WO 01/09302 A2 | 2/2001 |
| WO | WO 01/44459 A2 | 6/2001 |
| WO | WO 2010/151634 A1 | 12/2010 |
| WO | WO 2011/163292 A1 | 12/2011 |

OTHER PUBLICATIONS

Cheng et al. (In Vitro Cellular & Developmental Biology-Plant 39.6 (2003): 595-604). (Year: 2003).*
Kaur et al. (Indian Journal of Biotechnology, vol. 8, (2009) pp. 332-334). (Year: 2009).*
Sigma Product Information Sheet dated Oct. 21, 1996. (Year: 1996).*
Joyce et al. (Plant Cell Rep (2010) 29:173-183). (Year: 2010).*
Thapa et al. (Field Crops Research 112 (2009) 124-130). (Year: 2009).*
Spomer et al. (In Vitro Cellular & Developmental Biology-Plant 32.3 (1996): 210-215). (Year: 1996).*
Jimenez. 2001. Regulation Of In Vitro Somatic Embryogenesis With Emphasis On The Role Of Endogenous Hormones. Revista Brasileira De Fisiologia Veget al, vol. 13, pp. 196-223.
Suprasanna et al. 2005. Regulation Of Somatic Embryogenesis By Plant Growth Regulators In Sugarcane. Sugar Tech, vol. 7, pp. 123-128.
Lakshmanan et al. 2006. Developmental And Hormonal Regulation Of Direct Shoot Organogenesis And Somatic Embryogenesis In Sugarcane (*Saccharum* Spp. Interspecific Hybrids) Leaf Culture. Plant Cell Reports, vol. 25, pp. 1007-1015.
Snyman et al. 2011. Applications Of In Vitro Culture Systems For Commercial Sugarcane Production And Improvement. In Vitro Cellular And Developmental Biology Plant, vol. 47, pp. 234-249, 2011.
Desai et al. 2004. Simple and Reproducible Protocol For Direct Somatic Embryogenesis From Cultured Immature Inflorescence Segments of Sugarcane. Current Science, Bangalore, vol. 87, pp. 764-768.
Cooke et al. 1993. The Role Of Auxin In Plant Embryogenesis. The Plant Cell, vol. 5, pp. 1494-1495, 1993.
Garcia et al. 2007. In Vitro Morphogenesis Patterns From Shoot Apices Of Sugarcane Are Determined By Light And Type Of Growth Regulator. Plant Cell, Tissue and Organ Culture, vol. 90, pp. 181-190.
Watt et al. 2009. In Vitro Minimal Growth Storage Of *Saccharum* Spp. Hybrid (Genotype 88H0019) At Two Stages Of Direct Somatic Embryogenic Regeneration. Plant Cell, Tissue and Organ Culture, vol. 96, pp. 263-271.

(Continued)

*Primary Examiner* — Charles Logsdon
(74) *Attorney, Agent, or Firm* — Crowell & Moring LLP

(57) ABSTRACT

There are provided compositions and methods for transforming plants, preferably monocot, and even more preferably, sugarcane. The transformation methods involve infection of plant tissue with *Agrobacterium*, and co-cultivation using culture medium comprising high concentrations of gelling agent, with the result of inhibiting the exacerbated growth of the bacteria and increasing the transformation frequencies. The invention includes regenerating transformed plants, and the transformed plants themselves.

12 Claims, 9 Drawing Sheets

(56) References Cited

OTHER PUBLICATIONS

Suprasana et al. 2010. Profiling Of culture-induced Variation In Sugarcane Plants Regenerated Via Direct And Indirect Somatic Embryogenesis By Using Transposon-Insertion Polymorphism. Sugar Tech, vol. 12, pp. 26-30.
Van Der Vyver, C. 2010. Genetic Transformation Of The Euploid Saccharum Officinarum Via Direct And Indirect Embryogenesis. Sugar Tech, vol. 12, pp. 21-25.
Basnayake et al. 2011. Embryogenic Callus Proliferation And Regeneration Conditions For Genetic Transformation Of Diverse Sugarcane Cultivars. Plant Cell Reports, vol. 30, pp. 439-448.
Ali et al. 2008. An Efficient Protocol For Large Scale Production Of Sugarcane Through Micropropagation. Pakistan Journal Of Botany, vol. 40, pp. 139-149.
Nieves et al. 2008. Effect Of Exogenous Arginine On Sugarcane (*Saccharum* Sp.) Somatic Embryogenesis, Free Polyamines And The Contents Of The Soluble Proteins And Proline. Plant Cells, Tissue And Organ Culture, vol. 95, pp. 313-320.
Kaur & Gosal. 2009. Desiccation of Callus Enhances Somatic Embryogenesis And Subsequent Shoot Regeneration In Sugarcane. Indian Journal Of Biotechnology, vol. 8, pp. 332-334.
Goel et al. 2010. In Vitro Morphogenesis In Leaf Sheath Explants Of Sugarcane Hybrid Var. Cos 99259. Sugar Tech, vol. 12, pp. 172-175.
Wamaitha et al. 2010. Thidiazuron-Induced Rapid Shoot Regeneration Via Embryo-Like Structure Formation From Shoot Tip-Derived Callus Culture Of Sugarcane. Plant Biotechnology, vol. 27, pp. 365-368.
Stachel et al. 1985. Identification Of The Signal Molecules Produced By Wounded Plant Cells That Activate T-DNA Transfer In Agrobacterium Tumefaciens. Nature, London, vol. 318, pp. 624-629.
Sheng & Citovsky. 1996. Agrobacterium-Plant Cell DNA Transport: Have Virulence Proteins, Will Travel. The Plant Cell, Baltimore, vol. 8, pp. 1699-1710.
Zambryski. 1992. Chronicle From The Agrobacterium-Plant Cell DNA Transfer Story. Annual Review Of Plant Physiology And Plant Molecular Biology, Palo Alto, vol. 43, pp. 465-490.
D'Hont & Glaszmann. 2005. Unraveling The Genome Structure Of Polyploids Using FISH And GISH; Examples Of Sugarcane And Banana. Cytogenetic And Genome Research, Basel, vol. 109, No. 1-3, pp. 27-33.
Irvine 1984. The Frequency Of Marker Change In Sugarcane Plants Regenerated From Callus Culture. Plant Cell, Tissue And Organ Culture, Dordrecht, vol. 3, No. 3, pp. 201-209.
Chen et al. 1987. Transformation Of Sugarcane Protoplasts By Direct Uptake Of A Selectable Chimeric Gene. The Plant Cell Reports, New York, vol. 6, pp. 297-301.
Bower & Birch. 1992. Transgenic Sugarcane Plants Via Microprojectile Bombardment, The Plant Journal, Oxford, vol. 2, No. 3, pp. 409-416.
Rathius & Birch, R. G. 1992. Stable Transformation Of Callus From Electroporated Sugarcane Protoplasts. Plant Science, Amsterdam, vol. 82, pp. 81-89.
Smith et al. 1992. Transient Expression Of The Coat Protein Of Sugarcane Mosaic Virus In Sugarcane Protoplasts And Expression In *Escherichia coli*. Archives of Virology, Vienna, vol. 125, pp. 15-23.
Gambley et al. 1993. Microprojetile Transformation Of Sugarcane Meristems And Regeneration Of Shoots Expressing β-Glucuronidase. The Plant Cell Reports, New York, vol. 12, pp. 343-346.
Birch. 1997. Plant Transformation: Problems And Strategies For Practical Application. Annual Review Of Plant Physiology And Plant Molecular Biology, Palo Alto, vol. 48, pp. 297-326.
Arencibia. 1998. An Efficient Protocol For Sugarcane (*Saccharum* Spp. L.) Transformation Mediated By Agrobacterium Tumefaciens. Transgenic Research, New York, vol. 7, pp. 213-222.
Enriquez-Obregon et al. 1998. Herbicide-Resistant Sugarcane (*Saccharum officinarum* L.) Plants By Agrobacterium-Mediated Transformation. Plant, Berlin, vol. 206, pp. 20-27.
Manickavasagam et al. 2004. Agrobacterium-Mediated Genetic Transformation And Development Of Herbicide-Resistant Sugarcane (*Saccharum* Species Hybrids) Using Axillary Buds. The Plant Cell Reports, New York, vol. 23, No. 3, pp. 134-143.
Rathus & Birch. 1992. Stable Transformation Of Callus From Electroporated Sugarcane Protoplasts. Plant Science, Amsterdam, vol. 82, pp. 81-89.
Dong et al. 2005. Comparative Plant Genomics Resources At PlantGDB[1]. Plant Physiology, Rockville, vol. 139, pp. 610-618.
Negrotto et al. 2000. The Use Of Phosphomannose-Isomerase As a Selectable Marker To Recover Transgenic Maize Plants (*Zea mays* L.) Via Agrabacterium Transformation. Plant Cell Reports vol. 19, pp. 798-803.
De La Riva et al. 1998. Agrobacterium Tumefaciens: A Natural Tool For Plant Transformation. Electron. J. Biotechnology, vol. 1, pp. 118-133.
Opabode. 2006. Agrobacterium-Mediated Transformation Of Plants: Emerging Factors That Influence Efficiency. Biotechnology Molecular Biology Review, vol. 1, pp. 12-20.
Hooykaas. 1989. Transformation Of Plant Cells Via Agrobacterium. Plant Mol. Biol., vol. 13, pp. 327-336.
Chilton. 1993. Agrobacterium Gene Transfer: Progress On A "Poor Man's Vector" For Maize Proc. Natl. Acad. Sci. USA, vol. 90, pp. 3119.
Ishida et al. 1996. High Efficiency Transformation Of Maize (*Zea mays* L.) Mediated By Agrobacterium Tumefaciens. Nature Biotechnology, vol. 14, pp. 745-750.
Komari et al. 1996. Vectors Carrying Two Separate T-DNAs For Co-Transformation of Higher Plants Mediated By Agrobacterium Tumefaciens And Segregation Of Transformants Free From Selection Markers. Plant Journal, vol. 10, pp. 165-174.
Murray et al. 1989. Codon Usage In Plant Genes. Nucleic Acids Res., vol. 17, pp. 477-498.
Ho & Vasil. 1983. Somatic Embryogenesis In Sugarcane (*Saccharum officinarum* L.) 1. The Morphology And Physiology Of Callus Formation And The Ontogeny Of Somatic Embryos. Protoplasma, vol. 118, pp. 169-180.
Brisibe et al., 1993. Developmental Electron Microscopy And Histochemistry Of Somatic Embryo Differentiation In Sugarcan. Plant Science, vol. 89, pp. 85-92.
Hood et al., 1993. New Agrobacterium Helper Plasmids For Gene Transfer To Plants. Transgenic Research, vol. 2, pp. 208-218.
International Search Report (PCT/ISA/210) issued in PCT Application No. PCT/BR2015/050154 dated Oct. 26, 2015 with English translation (Six (6) pages).
Portuguese-language Written Opinion PCT/ISA/237) issued in PCT Application No. PCT/BR2015/050154 dated Oct. 26, 2015 (Five (5) pages).

\* cited by examiner

METHOD FOR TRANSFORMING A PLANT CELL OR PLANT TISSUE USING AGROBACTERIUM, TRANSGENIC PLANT, TRANSGENIC CELL OR TRANSGENIC TISSUE, CULTURE MEDIUM AND USE OF A METHOD FOR TRANSFORMING A PLANT CELL OR TISSUE

FIELD OF THE INVENTION

The present invention pertains generally to plant biotechnology. More specifically, the invention pertains to methods of transforming plants mediated by *Agrobacterium*.

BACKGROUND OF THE INVENTION

Sugarcane (*Saccharum* spp.) is a grassy plant belonging to the botanic family Poaceae, originating from Southeast Asia, from the large central region of New Guinea and Indonesia (Daniels & Roach, 1987, Sugarcane improvement through breeding p. 7-84). It is one of the most important plant species cultivated in tropical and subtropical regions, with an area exceeding 23 million hectares distributed over 121 countries (FAO Statistical Yearbook 2012 p. 233).

The sugarcane cultivated area is on the increase, and it is a source of raw materials for the production of sugar, wine, molasses, ruin, cachaça (the national distilled of Brazil) and fuel ethanol. The bagasse remaining after milling the sugarcane can be used for balering and supply of heat energy, used in mill, and electricity, which is typically sold to the consumer electrical grid, and as a base for producing ethanol. Therefore, the sugarcane agroindustry, responsible for generating millions of jobs in the area, is of major social importance, generating revenue through the export of sugar and ethanol and by the rational use of the plant biomass.

More recently, with increased concern over global warming and use of alternative sources to fossil fuels (biofuels), world interest in sugarcane has increased significantly.

Due to the economic and social importance of sugarcane, major research efforts are noted, aimed at defining better agricultural practices for cultivation and improved quality of the varieties cultivated.

In this regard, conventional plant breeding methods have proven limited for the introduction of genes and traits of interest in different varieties of commercial interest.

Due to this difficulty and the growing need to incorporate desirable traits, such as, for example, increased productivity, tolerance to insects, pathogen and herbicides, resistance to abiotic stresses, etc., molecular biology methods have been used to manipulate sugarcane.

The genetic engineering of plants involves the transfer of genes of interest into the plant cells, such that a fertile and agronomically superior progeny that maintains and expresses in a stable manner the exogenous gene can be obtained. Accordingly, one of the options is the use of in vitro cultivation techniques.

One of the techniques of in vitro cultivation is somatic embryogenesis, which consists of the production of embryos from an isolated cell or a small group of cells which, by means of in vitro cultivation will give rise to somatic embryos. In this case, structures similar to zygotic embryos develop from somatic cells, following a sequence of characteristic stages of zygotic embryogenesis, giving rise to a plant, without the fusion of gametes (Jimenez. 2001. Regulation of in vitro somatic embryogenesis with emphasis on the role of endogenous hormones. Revista Brasileira de Fisiologia Vegetal, v. 13, p. 196-223).

According to Guerra et al., Embriogênese somática e sementes sintéticas. In: Tones et al. (Eds.). 1999. Cultura de tecidos e transformação genética de plantas. Brasilia: Embrapa, v.2, p. 533-568, a striking characteristic of somatic embryos is the presence of a closed vascular system, without vascular connection with the tissues of the initial explant. This characteristic coupled with its bipolarity (presence of shoot and root apices), enables the distinction between the processes of embryogenesis and organogenesis (Falco et al. 1996. Histological characterization of in vitro regeneration of *Saccharum* sp. Revista Brasileira de Fisiologia Vegetal, v.9, p. 93-97).

According to Suprasanna et al. (2005. Regulation of somatic embryogenesis by plant growth regulators in sugarcane. Sugar tech, v. 7, p. 123-128), the use of somatic embryogenesis in the cultivation of sugarcane has two main objectives: the development of a reproducible method for the fast propagation of plants and the achievement of an efficient system of regeneration of somatic embryos used for genetic transformation.

Various types of explants have been used in the embryonic process in sugarcane. According to Lakshmanan et al. (2006. Developmental and hormonal regulation of direct shoot organogenesis and somatic embryogenesis in sugarcane (*Saccharum* spp. Interspecific hybrids) leaf culture. Plant Cell Reports, v. 25, p. 1007-1015), almost all plant tissues give rise to embryogenic calluses, but the younger leaves (Chengalrayan & Gallo-Meagher. 2001. In vitro Cellular and Developmental Biology-Plant, Oxon, v. 37, p. 434-439; Lakshmanan et al. 2006. Developmental and hormonal regulation of direct shoot organogenesis and somatic embryogenesis in sugarcane (*Saccharum* spp. Interspecific hybrids) leaf culture. Plant Cell Reports, v. 25, p. 1007-1015; Snyman et al. 2011. Applications of in vitro culture systems for commercial sugarcane production and improvement. In vitro Cellular and Developmental Biology Plant, v. 47, p. 234-249, 2011) and developing inflorescences (Gallo-Meagher et al. 2000. Thidiazuron stimulates shoot regeneration of sugarcane embryogenic callus. In vitro Cellular and Developmental Biology Plant, v. 36, p. 37-40); Desai et al. 2004. Current Science, Bangalore, v. 87, p. 764-768), are very prolific and are preferred target tissues for fast production of embryogenic calluses.

Somatic embryogenesis is initiated by adding growth regulators to the culture medium and, among these, the auxins stand out as the class of growth regulators most used in the embryonic process (Cooke et al. 1993. The role of auxin in plant embryogenesis. The Plant Cell, v. 5, p. 1494-1495, 1993). The 2,4D (2,4-dichlorophenoxyacetic acid) is the growth regulator most used in the induction process of somatic embryogenesis in sugarcane.

The conversion of the somatic embryos in plants is the final phase of the process of somatic embryogenesis. Regeneration generally occurs in a medium devoid of growth regulators and in the presence of light (Garcia et al. 2007. In vitro morphogenesis patterns from shoot apices of sugarcane are determined by light and type of growth regulator. Plant Cell, Tissue and Organ Culture, v. 90, p. 181-190; Watt et al. 2009. In vitro minimal growth storage of *Saccharum* spp. Hybrid (genotype 88H0019) at two stages of direct somatic embryogenic regeneration. Plant Cell, Tissue and Organ Culture, v. 96, p. 263-271; Suprasana, et al. 2010. Profiling of culture-induced variation in sugarcane plants regenerated via direct and indirect somatic embryogenesis by using transposon-insertion polymorphism. Sugar Tech, v.12, p. 26-30; Van Der Vyver, C. 2010. Genetic transformation of the euploid *Saccharum officinarum* via direct and indirect embryogenesis. Sugar tech, v. 12, p. 21-25; Basnayake et al. 2011. Embryogenic callus proliferation and regeneration conditions for genetic transformation of diverse sugarcane cultivars. Plant Cell Reports, v. 30, p. 439-448), however, this process may be improved by using different regulators (Ali et al. 2008. An efficient protocol for large scale production of sugarcane through micropropagation. Pakistan Journal of Botany, v.40, p. 139-149; Nieves et al. 2008. Effect of exogenous arginine on sugarcane (*Saccharum* sp.) somatic embryogenesis, free polyamines and the contents of the soluble proteins and proline. Plant Cells, Tissue and Organ Culture, v. 95, p. 313-320; Kaur & Gosal. 2009. Callus desiccation enhances somatic embryogenesis and subsequent shoot regeneration in sugarcane. Indian Journal of Biotechnology, v. 8, p. 332-334; Goel et al. 2010. In vitro morphogenesis in leaf sheath explants of sugarcane hybrid var. CoS 99259. Sugar Tech, v. 12, p. 172-175; Wamaitha et al. 2010. Thidiazuron-induced rapid shoot regeneration via embryo-like structure formation from shoot tip-derived callus culture of sugarcane. Plant Biotechnology, v. 27, p. 365-368).

Recombinant DNA technology has enabled the isolation of genes and the stable insertion into a host genome (Quecini & Vieira.2001. Plantas transgênicas. In: Serafini et al. (Ed.). Biotecnologia na agricultura e na agroindústria. Guaíba: Agropecuária, p. 278-331). This technique, also called genetic transformation, may be defined as the controlled introduction of nucleic acids (DNA) in a host genome, excluding the introduction by fecundation. It is a more controlled process, where normally only the defined DNA fragment is introduced into the host genome, or receptor genome, and must be integrated thereto (Brasileiro & Dusi. 1999. Transformação genética de plantas. In: Torres et al. (Ed.) Cultura de tecidos e transformação genética de plantas. Brasilia: EMBRAPA-SPI/EMBRAPA-CNPH, 863p, v.2). The stable insertion of these molecules into a host genome gives rise to an individual identical to the receptor of the recombinant molecule, but with the addition of a new and particular characteristic (Quecini & Vieira, 2001, above).

There are various techniques of genetic transformation of plants grouped into two categories: indirect and direct transfer of genes. Indirect transfer is the one in which the exogenous DNA is inserted into the genome by the action of a biological vector, whereas direct transfer is based on physical-biochemical processes.

Indirect transformation is chiefly based on the system mediated by bacteria of the genus *Agrobacterium* and has been the most used method to obtain transgenic plants. *Agrobacterium tumefaciens* and *A. rhizogenes* are phytopathogenic soil bacteria, grain negative, belonging to the Rhizobiaceae family, which cause diseases in dicot, known as crown galls and hairy root, respectively. In this plant-pathogen interaction there occurs a process of natural transfer of genes between the agrobacteria and the plant cell, when bacterial DNA fragments (T-DNA) are transferred into the plant cell, integrating the nuclear genome (Ream & Gelvin. 1996. Crown gall: Advances in understanding interkingdom gene transfer. Saint Paul: APS Press, 148p). In its natural form, the bacteria transfers the T-DNA ("transferred DNA"), which is the part of the bacterial plasmid called Ti ("tumor-inducing"), and this integrates the genome of the infected plant cells. In the T-DNA fragment that is transferred to the plant cell are the genes involved in the phytohormone-constituting biosynthesis (auxins and cytokines) that alter the program of normal development of the infected tissue, causing the formation of the tumor. Additionally, it also contains oncogenes for the synthesis of sugars and amine acids called opines, which are responsible for the survival of the bacteria, which use them as a source of carbon and nitrogen (Oger et al. 1997. Genetically engineered plants producing opines alter their biological environment. Nature Biotechnology, New York, v. 15, p. 369-372).

Repeated ends of 25 base pairs (bp) on the right and left edges delimit the T-DNA and are essential for the transfer thereof (Wang et al. 1984. Cell, Cambridge, v. 38, p. 455-462). Phenolic compounds released by the wounded plant tissues activate specific regions (vir), initiating the T-DNA transfer process to the plant cell (Stachel et al. 1985. Identification of the signal molecules produced by wounded plant cells that activate T-DNA transfer in *Agrobacterium tumefaciens*. Nature, London, v. 318, p. 624-629). The *Agrobacterium* also has chromosomal genes (chv) that assure the link between the bacterial and host cells, enabling the formation of the passage pore of the T-strand complex (Sheng & Citovsky. 1996. *Agrobacterium*-plant cell DNA transport: have virulence proteins, will travel. The Plant Cell, Baltimore, v.8, p. 1699-1710).

The virulence region, called vir region is responsible for the transfer process, and the induction process and transfer of strand—T is controlled by the coordinated expression of this region. The virA locus encodes a membrane protein that perceives the presence of metabolites of the wounded plant (acetosyringone). After bonds to acetosyringone, the "activated" VirA protein modifies the VirG protein, which is also expressed constitutively, but on a lower scale through phosphorylation thereof. The phosphorylated VirG protein is responsible for inducing the transcription of the entire vir region. To form the T-strand, the operon virD encodes endonucleases capable of recognizing and cleaving inside the 25 bp which delimit the region-T. The transfer of the T-strand is polar, always from right to left. The T-strand is transferred to the plant cell in the form of a single strand, protected in 5'portion of the molecule by the protein VirD2, and throughout the T-strand by protein VirE2 (Zambryski. 1992. Chronicle from the *Agrobacterium*-plant cell DNA transfer story. Annual Review of Plant Physiology and Plant Molecular Biology, Palo Alto, v. 43, p. 465-490). The T-DNA released is protected by bonds throughout the single strand by the protein VirE2, which is also responsible for the structural organization of the strand during the path between the bacterial cell and the plant cell. Encoded proteins by the locus virB assure the passage through the membrane of the bacteria, by the formation of passage pore between the membrane and the cell wall (Zambryski, 1992, above).

The process of transfer may be split into two main steps: a bacterial step and an eukaryotic step that occurs in the plant cell (Zupan & Zambryski. 1995. Plant Physiology, Rockville, v. 107, p. 1041-1047). The bacterial step includes the production and export of a functional vector containing the genetic information of the T-DNA (Tinland. 1996. The integration of T-DNA into plant genomes. Trend in Plant Science, Kidlington, v. 1, p. 178-183). The eukaryotic step includes the recognition between the *Agrobacterium* and the host cell, the transduction of plant signals of pathogenesis and the activation of the vir genes (Sheng & Citovsky. 1996, above). Since the segment to be transferred is defined by its edges, the encoding region of the wild-type T-DNA may be replaced by any other DNA sequence without impairing its transfer from *Agrobacterium* to the plant. The replacement of the oncogenes by genes of interest, flanked by the edges of the T-DNA, provides an efficient system of obtaining transgenic plants (Brasileiro & Dusi. 1999, above).

The vectors used for the transformation via *A. tumefaciens* are called "disarmed", that is, they do not have the oncogenes in their plasmid, but retain the virulence genes (vir region), located in the plasmid Ti (Ream & Gelvin. 1996. Crow gall: advances in understanding interkingdom gene transfer. Saint Paul: APS Press, 148p). These plasmid constructions have plant promoters and bacterial genes that confer resistance to antibiotics, making these markers efficient for the selection of cells or transformed plants. Therefore, *A. tumefaciens* is used as transformation vector, where the T-DNA fragment is eliminated and replaced by a gene of interest (Saciloto. 2003. Insertion of the PR5K gene in sugarcane with a view to inducing resistance to the *Puccinia melanocephala* rust fungus. 74p. Master's dissertation presented before the Luiz de Queiroz Superior School of Agriculture, University of São Paulo, Piracicaba), losing the capacity to cause tumors, but being capable of transferring the exogenous DNA. Explants inoculated with the disarmed strains have a regenerative capacity and large production percentage of transgenic plants (Brasileiro. 1998. Manual de transformação genética de plantas. Brasília: EMBRAPA, CENARGEN, 309p).

The complexity of the polyploid and aneuploid genome of sugarcane varieties (D'Hont & Glaszmann. 2005. Unraveling the genome structure of polyploids using FISH and GISH; examples of sugarcane and banana. Cytogenetic and Genome Research, Basel, v. 109, n. 1-3, p. 27-33), added to its relatively restrict genetic basis, imposes major difficulties to the application of conventional plant breeding techniques. Considered this situation, biotechnology may be applied in plant breeding programs to overcome or reduce some of the limitations of conventional approaches, and increase the productivity of sugarcane biofuel. For this, certain characteristics can be incorporated to the culture by way of genetic engineering through the genetic transformation of plants, to reduce the losses with biotic stresses associated with pests, plant weeds and diseases, and abiotic stresses related to drought, cold, salinity among others. Biotechnology can also make changes to optimize the content and the quality of sugar (Melotto-Passarin. (2009). Doctorate Thesis in Physiology and Biochemistry of Plants presented at the "Luiz de Queiroz" Superior School of Agriculture, University of São Paulo, Piracicaba, 148p.).

Sugarcane presents characteristics that make it an excellent plant for improvement through genetic transformation, such as its facility for regenerating plants from calluses in vitro (Heinz et al. 1997. Cell, tissue and organ culture in sugarcane improvement. In: Reinert & Bajaj (Ed.). Applied and fundamental aspects of plant cell, tissue and organ culture. Berlin: Springer Verlag, p. 3-17; Irvine 1984. The frequency of marker change in sugarcane plants regenerated from callus culture. Plant Cell, Tissue and Organ Culture, Dordrecht, v. 3, n. 3, p. 201-209; Chen et al. 1988. Control and maintenance of plant regeneration in sugarcane callus cultures. Journal of Experimental Botany, Oxford, v. 39, p. 251-261) and, its multiplication mode on commercial scale by vegetative propagation that enables distribution of stable transformants to the producers through seedlings (Gallo-Meagher & Irvine. 1996. Herbicide resistant transgenic sugarcane plants containing the bar gene. Crop Science, Madison, v. 36, it 5, p. 1367-1374). In contrast, it does not allow the use of zygotic embryo as target tissue in the transformation, contrary to maize, rice, wheat and other commercial cereal crops.

Over the last decade, various researches have been carried out to develop efficient methods of genetic transformation of sugarcane (Chen et al. 1987. Transformation of sugarcane protoplasts by direct uptake of a selectable chimeric gene. The Plant Cell Reports, New York, v.6, p. 297-301; Bower & Birch. 1992. The Plant Journal, Oxford, v. 2, n. 3, p. 409-416; Rathius & Birch, R. G. 1992. Stable transformation of callus from electroporated sugarcane protoplasts. Plant Science, Amsterdam, v. 82, p. 81-89; Smith et al. 1992. Transient expression of the coat protein of sugarcane mosaic virus in sugarcane protoplasts and expression in *Escherichia coli*. Archives of Virology, Vienna, v. 125, p. 15-23; Birch & Maretzki, A. 1993. Transformation of sugarcane. In: Bajaj, Y. P. S. (Ed.). Plant protoplasts and genetic engineering IV. Biotechnology in Agriculture and Forestry. Heidelberg: Springer-Verlag, v. 23, p. 348-360; Gambley et al. 1993. Microprojetile transformation of sugarcane meristems and regeneration of shoots expressing β-glucuronidase. The Plant Cell Reports, New York, v. 12, p. 343-346; Gambley et al. 1994. Australian Journal of Plant Physiology, Melbourne, v. 21, p. 603-612; Birch. 1997. Plant transformation: problems and strategies for practical application. Annual Review of Plant Physiology and Plant Molecular Biology, Palo Alto, v. 48, p. 297-326; Arencibia. 1998. An efficient protocol for sugarcane (*Saccharum* spp. L.) transformation mediated by *Agrobacterium tumefaciens*. Transgenic Research, New York, v. 7, p. 213-222; Elliott et al. 1998. Australian Journal of Plant Physiology, Melbourne, v. 25, p. 739-743; Enriquez-Obregon et al. 1998. Plant, Berlin, v. 206, p. 20-27; Manickavasagam et al. 2004. *Agrobacterium*-mediated genetic transformation and development of herbicide-resistant sugarcane (*Saccharum* species hybrids) using axillary buds. The Plant Cell Reports, New York, v. 23, it 3, p. 134-143). Different transformation techniques using electroporation (Rathius & Birch. 1992. Stable transformation of callus from electroporated sugarcane protoplasts. Plant Science, Amsterdam, v. 82, p. 81-89), treatment with polyethylenoglycol (PEG) (Chen et al. 1987. Transformation of sugarcane protoplasts by direct uptake of a selectable chimeric gene. The Plant Cell Reports, New York, v.6, p. 297-301), microprojectile bombardment (Franks & Birch 1991. Gene transfer into intact cells using microprojectile bombardment. Australian Journal of Plant Physiology, Melbourne, v. 18, p. 471-480) and *Agrobacterium tumefaciens* (Arencibia. 1998. An efficient protocol for sugarcane (*Saccharum* spp. L.) Transformation mediated by *Agrobacterium tumefaciens*. Transgenic Research, New York, v. 7, p. 213-222; Elliott et al. 1998. *Agrobacterium*-mediated transformation of sugarcane using GFP as a screenable marker. Australian Journal of Plant Physiology, v. 25, p. 739-743) were used to introduce marker genes in cells and cane calluses. The first transgenic cane cells were obtained following the transfer of DNA for protoplasts mediated by PEG (Chen et al. 1987. Transformation of sugarcane protoplasts by direct uptake of a selectable chimeric gene. The Plant Cell Reports, New York, v.6, p. 297-301).

The first attempts at transforming sugarcane using *Agrobacterium tumefaciens*, with or without virulence gene inhibitors and other treatments that improve the infection, had little success (Birch & Maretzki. (1993). Transformation of sugarcane. In: Bajaj, Y.P.S. (Ed.). Plant protoplasts and genetic engineering IV. Biotechnology in agriculture and forestry. Heidelberg: Springer-Verlag, v. 23, p. 348-360). However, Arencibia (1998. An efficient protocol for sugarcane (*Saccharum* spp. L.) Transformation mediated by *Agrobacterium tumefaciens*. Transgenic Research, New York, v. 7, p. 213-222) was capable of regenerating morphologically normal transgenic sugarcane plants following the co-cultivation of calluses with *Agrobacterium tumefaciens* strains LBA4404 and EHA101. Almost simultaneously, Enriquez-Obregon et al. (1998, Plant, Berlin, v. 206, p. 20-27) reported the production of cane plants resistant to the commercial herbicide BASTA (active component phosphinothricine). However, few laboratories managed to repeat these pioneer works of agrobacteria in sugarcane at the time following the publications.

With suitable handling and control of the in vitro culture conditions, considering the best age, type and stage of the embryonic culture, and also the improvement of the virulence of the *A. tumefaciens* strain demonstrated enhanced transformation efficiency. This natural transformation model presents advantages of transferring relatively long DNA segments with no re-arrangement, integrating a small number of copies of the transgenes in genome sites with high expression rate, being a simple and low-cost methodology (Melotto-Passarin, 2009, above).

Besides producing good agricultural products, genetic transformation technology also offers the possibility of studying thousands of plant genes (with known and unknown functions) which have been identified by the countless genome programs conducted throughout the world over recent years (Dong et al. 2005. Plant Physiology, Rockville, v. 139, p. 610-618).

Although the transformation methods mediated by *Agrobacterium* are used for the genetic manipulation of sugarcane, it is broadly recognized by those skilled in the art that the efficiency and reproducibility of the methodologies also constitute challenges to be overcome. In any technology for transforming plants, there are multiple factors that influence the success of the transfer of a gene of interest in plants, and its subsequent stable integration and expression. One of the aspects that might affect the transformation success is the growth of *Agrobacterium* in relation to transformed plant cells. It is known that if there is exacerbated growth of *Agrobacterium*, the chances of regenerating plants from transformed cells decreases. This may be due to the necrosis induced by *Agrobacterium*, in a process in which the tissue firstly undergoes a process of oxidation and browning and subsequently dies.

The inoculation of a plant tissue with *Agrobacterium* is, in itself, a process that unleashes hypersensitivity responses, resulting in a low survival rate of the tissue. Therefore, the planning of a suitable artificial environment to minimize the damages due to the interaction of the plant tissue with *Agrobacterium* is critical for the success of genetic transformation experiments.

Document WO 200109302 discloses control of the growth of *Agrobacterium* as a form of improving the efficiency of transformation, through the use of inhibitor agents during inoculation and co-culture of *Agrobacterium* with the plant tissue. Preferred inhibitor agents are compounds containing heavy metals, such as silver nitrate or silver thiosulphate, antibiotics such as carbenicillin and a combination of antibiotics and a clavulanic acid, such as augmentin or timetin.

Document U.S. Pat. No. 6,323,396 discloses a process for obtaining transgenic plants using mutant *Agrobacterium* deficient in the biosynthesis of vital specific biomolecules. This will enable the maintenance of a controlled systemic infection of the tissue to be transformed for long periods, increasing the likelihood of success in the infection. The *Agrobacterium* is eliminated by the omission of these nutrients from the incubation medium.

Document WO2010151634 discloses the co-cultivation in desiccant conditions, in the absence of culture medium, mentioning that this beneficially reduces the necrosis/apoptosis of the inoculated plant tissue, besides improving the subsequent cellular survival during the selection and regeneration steps which typically follow on from the co-cultivation step.

Document WO 98/54961 discloses antinecrotic treatments including cultivation in a necrosis inhibitor medium containing an ethylene or ethylene biosynthesis inhibitor, heat shock treatment of the cells or tissues before co-cultivation with *Agrobacterium* and transformation of the cells of grasses, chiefly maize, with genetic sequences such as p35, iap and dad-1.

Document WO 01/44459 describes agents that inhibit the activity or production of enzymes associated with the browning of plant tissues during the transformation mediated by *Agrobacterium*, such as polyphenol oxidase (PPO) and peroxidase (POD), metal chelators necessary for enzyme activity, and agents containing sulfhydryl (e.g. L-cysteine, cysteine, DTT, ascorbic acid, sodium thiosulfate and glutathione). The inhibited enzymes include oxidase (PPO) and peroxidase.

In view of this problem in the state of the art, the present invention provides a method of genetic transformation that contributes to the genetic plant breeding programs and functional studies of new genes, including those with complex multigene characteristics, by establishing new culture conditions during the co-culture of *Agrobacterium* with the plant tissue to be transformed, resulting in an improvement compared with existing methods. The inventors believe that the method presented herein, due to the advantages and unexpected effects obtained, may contribute to minimize the intrinsic limitations of the genetic breeding of plants of interest, including, but not limited to sugarcane.

SUMMARY OF THE INVENTION

In one aspect, the invention provides a method for transforming a plant cell or plant tissue using *Agrobacterium* comprising the steps of:
(a) contacting a plant cell or tissue with *Agrobacterium* containing at least a sequence of nucleotides of interest to be transferred to the plant cell or tissue;
(b) co-cultivating the plant cell or tissue in a co-cultivation medium capable of supporting the growth of the plant cell or tissue and inhibiting the growth of *Agrobacterium*;
(c) cultivating the cell or the tissue of step (b) in a medium comprising an agent capable of inhibiting the growth of *Agrobacterium*, and a selection agent to the transforming plant cell;
(d) selecting at least a transforming cell comprising the sequence of interest.

In one embodiment, the method additionally comprises regenerating transgenic plants.

In an additional embodiment, the transgenic plants are agronomically superior, in comparison with the non-transgenic plant of the same genotype.

In an embodiment, the co-cultivation medium comprises the use of concentrations of gelling agent above those recommended by the manufacturer, of agar, agargel, Phytablend™, Agargellan™, Phytagel™, Gelzan™, carrageenan and gellan gum.

In an additional embodiment, the concentration of gelling agent is over at least 10 g/L for agar or over at least 5 g/L agargel or over at least 5 g/L Agargellan or over at least 9 g/L of Phytablend™ or over at least 2.5 g/L of Phytagel™ or over at least 4 g/L of Gelzan™ or over at least 4 g/L of gellan gum or over at least 10 g/L of carrageenan.

In another embodiment, a plant cell or tissue to be transformed is from a monocot plant or from a dicot plant, in which the selected monocot plant may be rice, maize, wheat, sorghum, oats, *Miscanthus,* barley, other grasses and sugarcane.

In another aspect, the invention provides a transgenic plant, transgenic cell or transgenic tissue produced by a method as defined above. In one embodiment, the transgenic plant is sugarcane.

In another additional aspect, the invention provides a culture medium comprising the use of concentrations of gelling agent above those recommended by the manufacturer. In an embodiment, the culture medium comprises a greater concentration of gelling agent than that usually employed in the art. In an additional embodiment, the selected gelling agent is agar, agargel, Phytablend™, Agargellan™, Phytagel™, Gelzan™, carrageenan and gellan gum, in which the concentration of gelling agent is over at least 10 g/L for agar or over at least 5 g/L for agargel or over at least 5 g/L for Agargellan or over at least 9 g/L for Phytablend™ or over at least 2.5 g/L for Phytagel™ or over at least 4 g/L for Gelzan™ or over at least 4 g/L for gellan gum or over at least 10 g/L for carrageenan. In another embodiment, the co-cultivation medium is capable of inhibiting the exacerbated growth of *Agrobacterium* and the death of the tissue, and/or providing greater transformation frequency.

In another aspect, the invention provides the use of the method of transformation as provided above, for obtaining transgenic plants agronomically superior in comparison with a non-transgenic plant of the same genotype.

DETAILED DESCRIPTION OF THE INVENTION

Figures 1A, 1B:
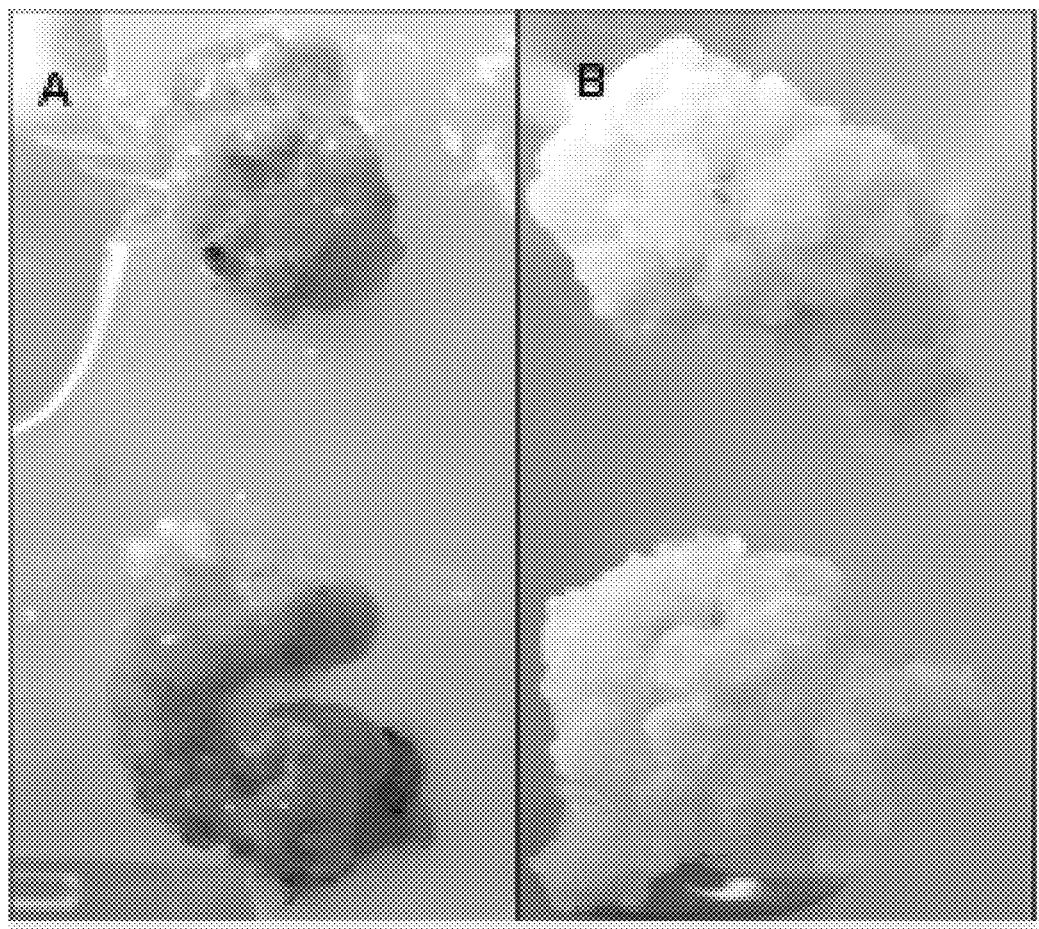
FIGS. 1A and 1B: Growth of *Agrobacterium* on the sugarcane calluses after three days of co-cultivation. A: co-cultivation in 7 g/L of agargel; B: co-cultivation in 28 g/L of agargel.

Unless defined otherwise, all the technical and scientific terms used herein have the same meaning as that understood by one skilled in the art to which the invention pertains. The purpose of the terminology used in the description of the invention is to describe particular embodiments only, and is not designed to limit the scope of the teachings. Unless indicated otherwise, all numbers expressing amounts, percentages and proportions, and other numerical figures used in the specification and in the claims, should be understood as being modified, in all cases, by the term "about". So unless indicated otherwise, the numerical parameters shown in the specification and in the claims are approximations that may vary, depending on the properties to be obtained.

There are provided compositions and methods mediated by *Agrobacterium* for transforming plants. The compositions include culture media comprising components known in the field of tissue culture, and high concentrations of gelling agent. The culture medium of the present invention is used in plant transformation methods, resulting in improved transformation efficiency and reduced tissue necrosis. Transformed plants, cells, tissues and seeds of transformed plants are also described herein.

The inventors of the present invention unexpectedly noted that the use of high concentrations of gelling agent in the process of transformation, notably in the co-cultivation step, result in lesser bacterial growth next to the inoculated plant tissue and, consequently, a lower rate of cellular death and enhanced transformation efficiencies.

In one aspect, a method for transforming plants, plant tissues or plant cells is provided. The methods provided herein are based on the gene transfer mediated by *Agrobacterium* to produce regenerative plant cells having a sequence of nucleotides of interest. As well understood, the transformation methods mediated by *Agrobacterium* exploit the natural ability of bacteria of the genus *Agrobacterium* to transfer DNA into plant chromosomes.

Plant transformation methods mediated by *Agrobacterium* are known in the art. Any suitable method for transforming plants, more preferably sugarcane, can be used in the method of the present invention. See for example WO 2010151634; WO 2011163292; U.S. Pat. No. 5,563,055; U.S. Pat. No. 5,981,840; WO 94/00977; U.S. Pat. No. 5,591,616, Negrotto et al. 2000. Plant Cell Reports 19: 798-803, Arencibia et al. 1998. Transgenic Res. 7:123-222; Arencibia & Carmona "Sugarcane (*Saccharum* spp.). 2007, In Methods in Molecular Biology, *Agrobacterium* Protocols, Vol. 2, ed. Wang ($2^{nd}$ ed., Humana Press, Inc.), pp. 227-235; de la Riva et al. 1998. Electron. J. Biotechnol. 1: 118-133; Manickavasagam et al. 2004. Plant Cell Rep. 23:134-143; Opabode. 2006. Biotechnol. Mol. Biol. Rev. 1 : 12-20; and Zhang et al. 2006. J Integr. Plant Biol. 48:453-459.

The method of the invention represents an improvement in the transformation of plants and obtainment of stably transformed plants, especially sugarcane, but not limited thereto, incorporating the use of culture media modified in the co-cultivation step.

Therefore, the methods for producing regenerable plant cells having a nucleotide sequence of interest generally comprise the steps of:

(a) contacting a tissue or a cell of a plant with *Agrobacterium* comprising a vector that comprises at least one expression cassette comprising the sequence of interest;

(b) co-cultivating said tissue or a said cell with said *Agrobacterium* in a support in the presence of a culture medium provided herein;

(c) cultivating said tissue or said cell of step (b) in a medium comprising an agent capable of inhibiting the growth of *Agrobacterium*, and a selection agent to the transforming plant cell; and (d) selecting at least a transforming cell comprising the sequence of interest.

Optionally, the method may additionally comprise a step of regenerating transgenic plants.

As used herein, "plant" refers both to the entire plant, a plant tissue, a plant part (such as embryo), a plant cell, or a group of plant cells. The class of plants that may be used in the method of the invention includes plants capable of being transformed by *Agrobacterium*, including both monocot and dicot. More preferably, the plants are monocot, and even more preferably, are those used as food or energy generation, such as rice, maize, wheat, barley, millet, sorghum, rye, triticale, sugarcane and other species such as *Erianthus, Miscanthus, Narenga, Sclerostachya,* and *Brachypodium*. Included are all the genera of the Bambusoideae subfamilies (e.g., the genus *Bambusa*), Andropogonoideae (e.g. genus *Saccharum, Sorghum* and *Zea*), Arundineae (e.g. genus *Phragmites*), Oryzoideae (e.g. genus *Oryza*), Panicoideae (e.g. genera *Panicum, Pennisetum* and *Setaria*), Pooideae (Festuciadeae) (e.g. genera *Poa, Festuca, Lolium, Trisetum, Agrostis, Phleum, Dactylis, Alopecurus, Avena, Triticum, Secale,* and *Hordeum*). More specifically, a plant that may be transformed according to the present invention is sugarcane. "Sugarcane" is understood to be a plant of the genus *Saccharum* L., preferably the species *Saccharum officinarum, S. spontaneum, S. robustum, S. barberi, S. sinense, S. edule, S. aegyptiacum, S. esculentum, S. aenicol, S. arundinaceum, S. bengalense, S. biflorum, S. ciliare, S. cylindricum, S. elephantinum, S. exaltatum, S. fallax, S. floridulum, S. giganteum, S. japonicum, S. koenigii, S. laguroides, S. munja, S. narenga, S. paniceum, S. pophyrocoma, S. purpuratum, S. ravennae, S. roseum, S. sanguineum, S. sara, S. chinense, S. tinctorium, S. versicolor, S. violaceum*. Even more preferably, these are interspecific hybrids produced by cross-breeding commercial species and varieties thereof.

A "control" or "plant control" provides a reference point for measuring the changes in the phenotype in the plant or genetically altered plant cell. It may comprise, for example: (a) a wild-type plant or cell, that is, having the same genotype as the start-up material for the genetic alteration which resulted in the altered plant or cell; (b) a plant or cell of the same genotype as the start-up material but which was transformed with a null construction (that is, with a construction that does not have a known effect in relation to the trait of interest); (c) a plant or plant cell which is a non-transformed segregant inside the progeny of an altered plant or plant cell; (d) a plant or plant cell genetically identical to the plant or plant cell but which was not exposed to conditions or stimuli that induced the expression of the gene of interest; or (e) plant or plant cell per se, under conditions in which the gene of interest is not expressed.

In step a) the cell or the plant tissue is placed in contact with *Agrobacterium*. This is the inoculation phase and may be for at least about one minute up to about 12 hours, more preferably from about 5 minutes to about 2.5 hours, even more preferably from about 25 minutes to about 40 minutes at room temperature and with or without stirring. During the inoculation, it is possible to apply some treatments to assist the infection, such as, for example, vacuum infiltration and sonication of the solution of *Agrobacterium*. For example, in the vacuum infiltration, the tissue or the plant cell in contact with the bacterial suspension is subjected to a vacuum pressure, preferably from −300 mmHg to −1000 mmHg, more preferably from 400 mmHg to 800 mmHg, even more preferably from −500 mmHg to −700 mmHg, usually for a period of 1 to 10 minutes, more preferably from 1 to 7 minutes, even more preferably from 1 to 5 minutes. In another non-limitative example, the vacuum infiltration occurs in vacuum pressure of −700 mmHg for 5 minutes. Further in this inoculation phase, to improve the transformation efficiency, it is possible to incorporate additives such as acetosyringone and surfactants inside the suspension of *Agrobacterium*.

Optionally, in some embodiments, before step a) described above, the cell or the plant tissue to be infected may be subjected to a temperature shock pre-treatment, in which said tissue or cell is placed in a liquid plant culture medium such as Murashige and Skook, Gamborg's, Chu ($N_6$), Schenk and Hildebrand, and other known by those skilled in the art, pre-heated at the temperature in which the heat shock pre-treatment will be conducted. The tissue or plant cell is then incubated in an incubator or water heating bath at a temperature above the temperature at which the inoculation will occur (for example, room temperature). So for example, the temperature of the temperature shock pre-treatment may occur at a temperature of about 30° C. to about 55° C., preferably from about 35° C. to about 50° C., even more preferably from about 40° C. to 45° C., for a period from about 1 minute to about 60 minutes, about 1 minute to about 50 minutes, about 1 minute to about 40 minutes, about 1 minute to about 30 minutes, about 1 minute to about 20 minutes, about 1 minute to about 15 minutes, about 1 minute to about 10 minutes, or about 1 minute to about 5 minutes. In another non-limitative example, the temperature shock treatment comprises placing and keeping the tissue or plant cell in a liquid plant culture medium pre-heated to a temperature of about 45° C. for about 5 minutes.

After this time, the liquid culture medium is discarded and replaced by the suspension of *Agrobacterium* prepared as described below.

The useful concentration of *Agrobacterium* in the methods of the invention, in step a) above, may vary depending on the strain of *Agrobacterium* used, the tissue or cell to be transformed, the genotype to be transformed, among others. Although the concentration of *Agrobacterium* may vary, generally the $OD_{600}$ used ranges between about 0.001 to about 5, more preferably from about 0.05 to about 2, and even more preferably, from about 0.1 to about 1.0.

A variety of species of *Agrobacterium* is known in the art, which can be used in the methods of the invention. See for example, Hooykaas. 1989. Plant Mol. Biol. 13:327; Smith, et al. 1995. Crop Science 35:301; Chilton. 1993. Proc. Natl. Acad. Sci. USA 90:3119; Mollony et al. 1993. Monograph Theor Appl Genet NY, Springer Verlag 19:148, lshida et al. 1996. Nature Biotechnol. 14:745; Komari, et al. 1996. The Plant Journal 10:165. In a preferred embodiment of the present invention, examples of strains of *Agrobacterium* include, but are not limited to, LBA4404, EHA101, EHA105, AGL1, C58C1, GV3101, GV2260 and others. The strain of *Agrobacterium* used in the methods of the invention is modified to contain a gene or genes of interest, or a nucleic acid to be expressed in the transformed cells. The nucleic acid to be transferred to the plant cell is incorporated in the region-T and is flanked by edge sequences of the T-DNA. In the Ti plasmid, the region is distinct from the vir region, the functions of which are responsible for transfer and integration. Systems of binary vectors have been developed in which disarmed T-DNA manipulated to carry the foreign DNA and the vir functions are present in separate plasmids. Therefore, a modified T-DNA comprising foreign DNA (the nucleotide sequence to be transferred) is constructed in a small plasmid which is replicated in *E. coli*. This plasmid is transferred by triparent conjugation to *A. tumefaciens*, which contains a compatible plasmid carrying the virulence gene. The vir functions are provided in trans to transfer the T-DNA to the plant genome. Said binary vectors are useful in the practice of the present invention.

Therefore, it is evident that the transformation of plants may involve the construction of an expression cassette or an expression vector that will act in a particular cell. Said expression cassette or vector may comprise a DNA that includes a gene under the control of, or operably linked to, a regulatory element (for example, a promoter). The expression cassette or expression vector may contain one or more genes such as combinations of operably linked genes and regulatory elements. The vector may be a plasmid and can be used alone or in combination with other plasmids to provide transformed cells using transformation methods to incorporate the genetic sequences of interest inside the genetic material of a plant cell. The terms DNA or "heterologous" gene, "introduced", "foreign" or "transgenic" refer to a recombinant DNA sequence or a gene that does not occur naturally in the genome of the cell or target plant, or that occurs in the transformed target plant at a different location or in different association in the genome in relation to a non-transformed plant.

A vector comprising the nucleic acid of interest is introduced into an *Agrobacterium*. The term "introduced" means to provide a nucleic acid (e.g. a genic construction, expression cassette) in a eukaryotic or prokaryotic cell. "Introduced" includes reference to the stable or transient transformation methods, as well as cross-breeding. Therefore, "introduced" includes the incorporation into the genome of the cell (e.g. DNA of chromosome, plasmid, plastid, or mitochondria), converted into an autonomous replicon, or expressed transiently (e.g. Transfected mRNA). General molecular techniques used in the invention are provided, for example, by Sambrook et al. (eds.). 1989. Molecular Cloning: A Laboratory Manual, Cold Spring Harbor Laboratory Press, Cold Spring Harbor, NY.

By means of genetic transformation, a plant, preferably a sugarcane plant, may be modified to exhibit improved or superior agronomic characteristics, in relation to the non-transformed plants of the same genotype. For example, transgenic plants can be modified so as to express genes having resistance to diseases and insects, having tolerance to herbicides, which confer nutritional value, increase in the content of sucrose, of fibers, influence in the plant growth, tolerance to abiotic stresses, increased production of biomass, modification of content (composition/content) of lignin, sterility, among others.

When appropriate, the sequence of interest to be transferred to a plant may be modified to optimize the expression. For example, a sequence may be modified to improve expression in a monocot plant, more preferably, in sugarcane. Methods for synthetic optimization are available in the technique, for example, U.S. Pat. No. 5,380,831; U.S. Pat. No. 5,436,391 and Murray, et al. 1989. Nucleic Acids Res. 17:477-498. The preferred codons of the target plant can be determined from higher frequency codons in the target plants of interest. Other modifications can be made in order to increase the gene expression in the target plant, including, for example, the elimination of spurious polyadenylation signals, of exon-intron splice signals, of similar transposons repetitions, among others. The G-C content of the sequence may be adjusted to average levels to a given target plant, calculated having as reference the known genes expressed in the target plant. Further, the sequence may be modified so as to prevent hairpin structures in the mRNA.

The nucleic acid to be transferred may be contained inside the DNA constructions or expression cassettes. The construction or expression cassette will comprise a transcription initiation region linked to the nucleic acid of the gene of interest. Said expression cassette is provided with a plurality of restriction sites for insertion of the gene or genes of interest, so that they remain under transcription regulation of the regulatory regions. One or multiple expression cassettes can be used in the practice of the invention. The transcription initiation region, the promoter, may be native or homolog or foreign or heterologous to the host. As used herein, a chimeric gene comprises an encoding sequence operably linked to the transcription initiation region, which is heterologous to the encoding region. The cassette will include in the 5'-3' transcription direction: a transcriptional and translational initiation region, a DNA sequence of interest, a functional transcriptional and translation termination region in plants.

In addition to plant promoters, promoters derived from a variety of sources can be used efficiently in plant cells to express genes of interest. For example, bacterial promoters, such as the octopine synthase promoter, the nopaline synthase promoter, the manopine sinase promoter; promoters of viral origin, such as the promoters 35S and 19S of the cauliflower mosaic virus (CaMV), promoter of the bacilliform sugarcane virus and the like, can be used. Promoters derived from plants include, but are not limited to, the promoter of the small subunit of ribulose-1,6-biphosphate (RUBP) carboxylase, beta-conglycinin promoter, the phaseolin promoter, the alcohol dehydrogenase promoter (ADH), promoter of temperature shock proteins, promoter of the actin depolymerization factor (ADF), and tissue-specific promoters. The promoters may also contain certain elements that act as enhancers which may improve transcription efficiency. Typical enhancers include, but are not limited to, intron 1 of alcohol dehydrogenase (ADH) and intron 6 of ADH-1. Constitutive promoters may also be used. Constitutive promoters direct continuous gene expression in almost all cell types and almost all the time. Examples include, but are not limited to, promoters of actin, ubiquitin and CaMV 35S. Tissue-specific promoters are responsible for the gene expression in specific cells or tissue types. Examples of tissue-specific promoters which may be used include those that are active during a certain stage of plant development. Examples of such promoters include, but are not limited to, root-specific, pollen, leaf, embryo, among others.

Under certain circumstances it may be desirable to use an inducible promoter. An inducible promoter is responsible for expressing genes in response to a specific signal, such as physical stimulus (e.g. Heat shock genes), light (e.g. ribulose-bis-phosphate carboxylase 1.5), hormones (e.g. glucocorticoid), antibiotic (e.g. tetracycline), metabolites and stress (e.g. drought). Other functional transcription and translation elements in plants can be used, such as, for example, untranslated 5' leader sequences, 3' transcription termination sequence and polyadenylate addition signal sequences.

Plant expression cassettes can include at least one genetic marker, operably linked to a regulatory element (a promoter, for example) that enables transformed cells containing the marker to be either recovered via negative selection (that is, inhibiting the growth of cells that do not contain the selection marker gene) or via positive selection (that is, screening for the product produced by the genetic marker). Many of the genetic marker genes suitable for transforming plants are known and include, for example, genes that encode for enzymes which metabolically detoxify a selective chemical agent which may be an antibiotic or a herbicide, or genes that encode an altered target which may be sensitive to the inhibitor. Some methods of positive selection are known in the art. The gene selection marker may, accordingly, enable the selection of transformed cells while the growth of cells that do not contain the inserted DNA can be suppressed by the selection compound. The preference for one selection marker gene occurs at the discretion of the technician, but any one of the following selections markers can be used, as well as any other gene not listed here. Examples of selection markers include, but are not limited to, resistance or tolerance to kanamycin, hygromycin, bleomycin, G418, methotrexate, phosphinothricin (Bialaphos), imidazolinone, glyphosate, sulfonylureas and triazolopyrimidine herbicides, such as chlorosulforon, bromoxynil and dalapon.

In addition to the selection marker, it may be desirable to use a reporter gene. In some cases, a reporter gene can be used without the simultaneous use of a selection marker. Reporter genes are genes that typically do not offer any advantage to the organism or tissue receptor, and typically encode for a protein which provides a phenotypic change or enzymatic property. Suitable reporter genes include, but are not limited to, beta-glucuronidase gene (GUS), firefly luciferase or fluorescent proteins such as green fluorescent protein (GFP) or yellow fluorescent protein (YFP), described in U.S. Pat. No. 7,951,923.

The tissue to be in contact with *Agrobacterium* may be any one, such as, for example, sections or fragments of sett or sugarcane heart, leaf blade, axillary buds, stein, stein apex, leaf sheath, internodes, petioles, flower stalks, root or inflorescence. Suitably, the explant is a segment, a slice or section of tissue. More preferably, the tissue to be connected with *Agrobacterium* is embryogenic callus. More preferably, the embryogenic callus is of the type II or III. Embryogenic calluses can be formed from any suitable tissue of a plant, preferably from a sugarcane plant. The culture of tissues in sugarcane is well known and follows a conventional production model of calluses and regeneration of plants initially described by Ho & Vasil. 1983. Protoplasma, 118:169-180; Brisibe et al. 1993. Plant Science, 89:85-92, and further by Falco et al. 1996. R. Bras. Fisiol. Veg., 8(2):93-97. Preferably, it uses an immature tissue to initiate the callus, such as sugarcane heart or meristems. In some cases, the tissue may be injured or crushed prior to or simultaneously with the contact with *Agrobacterium* comprising a vector or expression cassette comprising the sequence of interest.

Thus, target cells include, but are not limited to, meristem cells, type I, type II and type III calluses, immature embryos and gametic cells, such as pollen, microspores, ovules and megaspores. Type I, II and III calluses can be initiated from tissues including, but not limited to, immature embryos, apex meristems, axillary meristems, microspores and others. Those cells capable of proliferating as calluses are also target cells for genetic transformation. Target cells can also be somatic cells, which are those cells that, during normal development of the plant, do not contribute to reproductive processes thereof. Meristem cells (that is, capable of continuous cell division and characterized by a undifferentiated cytological appearance, normally found at growing points as root tips, axillary meristems, shoot apices, side buds and others) may represent another type of target cell. Due to the undifferentiated state and capacity for differentiation and totipotency, a single transformed meristem cell can regenerate a whole transformed plant.

Suitable cell cultures can be initiated from various types of explants. For example, for varieties of sugarcane, explants can be obtained from suitable plant tissue, including sett or sugarcane heart (set of young and curled sheets containing apical meristem), leaf blade, axillary buds, stein, stein apex, leaf sheath, internodes, petioles, flower stalks, seeds, roots or inflorescence. Suitably, the explant is a segment, a slice or section of tissue. More preferably, the explant is a section of the apical sugarcane heart portion of sugarcane saplings. The explants can be obtained from plants grown in vitro, in greenhouses or in the field. Preferably, the plant age is less than about 24 months, less than about 23 months, less than about 22 months, less than about 21 months, less than about 20 months, less than about 19 months, less than about 18 months, less than about 17 months, less than about 16 months, less than about 15 months, less than about 14 months, less than about 13 months, less than about 12 months, less than about 11 months, less than about 10 months, less than about 9 months, less than about 8 months, less than about 7 months, less than about 6 months, less than about 5 months, less than about 4 months, less than about 3 months, less than about 2 months or less than about 1 month. Preferably, the plant age is preferably about 24-12 months, more preferably about 12-8 months, even more preferably about 4-6 months. Said tissue culture is generally initiated from sterile pieces of a plant, such as outlined above. Many explant characteristics are known to affect the efficiency of initiation of the culture, however, it is considered that generally young, faster-growing tissues, or a tissue in an earlier stage of development, are more efficient. Explants cultivated in appropriate media may give rise to an unorganized mass of dividing cells (calluses) that may, in culture, be maintained more or less undefine as long as periodic subcultures are carried out in a fresh culture medium.

The "co-cultivation" step (stage b, as defined above) refers to the incubation of the infected plant tissue or tissue which came into contact with *Agrobacterium* on a support, so as to enable the transfer of T-DNA of the *Agrobacterium* for the plant cells. This step corresponds to the period between the moment soon after inoculation (contact of the *Agrobacterium* with the plant tissue) to the moment when the bacteria is withdrawn or inactivated. In one embodiment, the co-cultivation of the plant tissue with *Agrobacterium* occurs on a culture medium as provided by the invention.

For purposes of this invention, "culture medium" refers to any media used in the art for supporting the viability and growth of a plant cell or tissue, or the growth of an entire plant, such as Murashige and Skook, Gamborg's, Chu (N6), Schenk and Hildebrand, and other known by those skilled in the art. Such media commonly include defined components, but not limited to: macronutrients, providing nutritional sources of nitrogen, phosphorus, potassium, sulfur, calcium, magnesium and iron; micronutrients, such as boron, molybdenum, manganese, cobalt, chlorine, iodine and zinc; carbohydrates, such as maltose, sorbitol and saccharide; phytohormones; vitamins; selection agents such as antibiotics or herbicides for selecting transformed cells or tissues; phenolic compounds (preferably those found in exudates of injury of plants, such as acetosyringone, sinapinic acid, syringic acid, ferulic acid, catechol, gallic acid, among others), antioxidants (for example, dithiotreitol), and gelling agents. It may also include complex components not defined, such as casein hydrolyzate, coconut water, yeast extract and activated carbon.

In one aspect, the culture media used in the co-cultivation step is referred to herein as "co-cultivation medium" and may be any culture medium of plant tissues known in the art and that comprises high concentrations of gelling agent. "Gelling agent" means any substance that increases the viscosity of a solution without substantially changing its properties, and include those gelling agents usually employed in plant tissue culture, such as agar, agargel, Phytablend™, Agargellan™, carrageenan and gellan gum (Gelzan™, Gelrite™, Phytagel™)

The co-cultivation medium of the invention provides support, moisture, nutrition to plant cells, at the same time in which it prevents the exacerbated growth of *Agrobacterium* and the death of the plant tissue. Accordingly, the culture medium of the invention comprises a greater concentration than that usually employed in the art of gelling agents. Without being limited to any theory or action mechanism, the inventors have surprisingly found that subjecting the inoculated tissue to a co-cultivation step in a co-cultivation medium comprising concentrations greater than that usually employed in the art of gelling agents, which usually correspond to the amounts recommended by the manufacturers, prevents the exacerbated growth of *Agrobacterium*, having the positive consequence of a lower mortality rate of the inoculated plant tissue and higher transformation frequencies. For the purposes of this invention, "high concentrations" means that the composition comprises at least amounts of use above those recommended by the manufacturer, defined herein as over at least 10 g/L for agar or over at least 5 g/L agargel or over at least 5 g/L Agargellan or over at least 9 g/L of Phytablend™ or over at least 2.5 g/L of Phytagel™ or over at least 4 g/L of Gelzan™ or over at least 4 g/L of gellan gum or over at least 10 g/L of carrageenan. More preferably, the concentration of agargel ranges from 7 to 70 g/L, more preferably from 7 to 60 g/L, and even more preferably from 7 to 50 g/L.

The inoculated tissue may be co-cultivated for about 1 to 30 days, preferably from 1 to 20, more preferably from 1 to 10, and even more preferably, from 1 to 5 days.

During the co-cultivation step, the temperature may be any suitable temperature for the target plant known in the art. Illustratively for sugarcane, the temperature may range from about 15° C. to about 30° C., from about 16° C. to about 29° C., from about 20° C. to about 25° C., from about 21° C. to about 24° C., or about 22° C. to about 23° C. In some embodiments, the co-cultivation step occurs in the absence of light.

Optionally, in some embodiments, after the co-culture step, the transformed cells can be subjected to a rest step. As used herein, "rest" refers to a step in which the plant cells, for example, embryogenic calluses, are incubated after the introduction of the sequence of interest by the infection mediated by *Agrobacterium*. The rest enables the preferred growth of a callus from transformed cells containing the sequence of interest, and is usually carried out in the absence of selective pressure. The transformed plant tissue is subjected to a rest medium that typically includes an agent (e.g. antibiotic) that inhibits the growth of *Agrobacterium*. Said agents are known in the art and include cefotaxime, timetin, vancomycin, carbenicillin and the like. The concentrations of said agent will vary according to the standard for each antibiotic. A person skilled in the art will recognize that the concentration of the inhibitor agent of *Agrobacterium* may be optimized for a particular transformation protocol without undue experimentation.

The rest step period may be from about 1 to about 30 days, preferably from about 1 to about 20 days, and even more preferably from about 5 to about 15 days. During the rest step, the temperature may be any suitable temperature for the target plant known in the art. Illustratively, for sugarcane, the temperature may vary from about 15° C. to about 30° C., from about 16° C. to about 29° C., from about 17° C. to about 28° C., from about 21° C. to about 27° C., or about 26° C. to about 27° C. In some embodiments, the rest step occurs in the absence of light.

When there is no rest step, it is possible to carry out an extended co-cultivation step, before adding the selective agent to the transformed plant cells.

The method provided herein further includes selecting the cells comprising at least one copy of the gene sequence of interest (step d). "Select", as used herein, means the situation in which a selective agent is used for the transformants, wherein said selective agent will enable the preferred growth of plant cells containing at least a copy of the gene marker positioned within the T-DNA and transferred by the *Agrobacterium* in detriment to those cells which were not transformed. As indicated above, any suitable selection marker can be used. In some embodiments, an agent is also added to inhibit the growth of *Agrobacterium*. The selection may occur in conditions of light or dark, depending on the plant species being transformed, and on the genotype, for example. In some cases, the embryogenic calluses or other tissues subjected to the transformation can be sub-cultivated at regular or irregular intervals in the same medium. In the case of transformation of calluses, it is possible to maintain separate individual calluses to ensure that only one plant is regenerated per callus and, therefore, all the regenerated plants are derived from independent transformation events. In a preferred embodiment, the selection step takes place in the dark, for about 1 to 10 weeks, more preferably from 2 to 5 weeks, even more preferably, from 2 to 4 weeks, and even more preferably, from 2 to 3 weeks.

After the selection period, the plant tissue that continued to grow in the presence of the selection agent, and which, therefore, was genetically modified, may be manipulated and regenerated, placing it in culture media and suitable growth conditions. The transgenic plants thus obtained can be tested for the presence of the DNA of interest. The term "regenerate", for purposes of this invention, refers to the formation of a plant, which includes an air part and roots. The regeneration of various species is well known in the art. Regenerated plants can be planted in suitable substrate, such as, for example, soil. As used herein, "genetically modified" or "transgenic" or "stably transformed" means a plant cell, plant part, plant tissue or plant comprising a DNA sequence of interest which is introduced into its genome by means of transformation.

For the present invention, "transformation efficiency" or "transformation frequency" may be measured by the number of cells transformed (or regenerated transgenic plants, or number of positive events) which are recovered under experiment conditions. For example, when calluses are used as start-up material for the transformation, the transformation frequency may be expressed as being the number of positive events obtained per grain of callus submitted to transformation.

The present invention is illustrated by the examples below, which are solely intended to exemplify one of the countless ways of realizing the invention, but without limiting the scope thereof. The various modifications or suggestions which can be proposed by one skilled in the art are included in the spirit and in the scope of the claims.

EXAMPLES

Example 1

Plant Material

Tissue culture is normally used for transforming plants by generating cells that are potentially transformable and apt for regenerating plants. Maintenance of tissue cultures requires the use of culture media (mixture of nutrients and phytoregulators for growth and maintenance of cells in vitro) and controlled environmental conditions. The tissue-explant used in this process of transforming sugarcane is the embryogenic callus.

To obtain the embryogenic calluses, young, curled leaves (heart) of sugarcane, developed in the field or greenhouse for 3-12 months, were collected for isolation of the initial explants.

After surface disinfection, cross sections about 0.05-5 mm thick were cut from the region above the meristem under aseptic conditions. The sections were placed on the surface of the SCIM culture medium. The cultures were kept in the dark at a temperature of 26° C.±2° C., and subcultivated every 15 days, for three to five cycles of 7-28 days. A week before the transformation, the calluses were again selected for the embryogenic characteristics (nodular, compact, opaque and slightly yellowish, slightly variable characteristics between the different genotypes).

Example 2

Preparation of the *Agrobacterium* and Infection of the calluses

The culture of *Agrobacterium*, comprising the strain EHA105 (Hood et al. 1993. New *Agrobacterium* helper plasmids for gene transfer to plants. Transgenic Research, v. 2, p. 208-218) with the genes UBIGUS/UBInptII, was initiated from a glycerol stock kept at −80° C. in solid LB plus appropriate antibiotics. This culture was kept in the dark at 28° C. for two to three days. The suspension of *Agrobacterium* to infect the plant material was prepared by resuspending the culture in a liquid medium ½ MS plus 200 µM of acetosyringone, adjusting to a final $OD_{600}$ of 0.1-1.0.

The calluses with embryogenicc characteristics were visually selected and directly transferred to the suspension of *Agrobacterium*, where they remained for 30 minutes, in the dark under constant stirring at 50 rpm.

After this period, the calluses were separated from the *Agrobacterium* and the excess suspension was removed by drying on sheets of filter paper.

Alternatively, prior to infection, the calluses can be subjected to a treatment in a ½ MS liquid medium at about 45° C. for about 5 minutes.

Another optional treatment is the submission of the infected plant material for about 5 minutes at vacuum pressure from about −700 mmHg.

Example 3

Co-Cultivation and Rest of the Calluses

This step was carried out in a liquid or solid SCIM culture medium (Table 1) with 7; 14; 21; 28; 35; 42 or 49 g/L of agargel, weighting between 0.5-10 g of callus per plate (100×20mm). The co-cultivation was carried out for a period of 1-5 days at a temperature of 22° C. in the dark.

Figure 3:
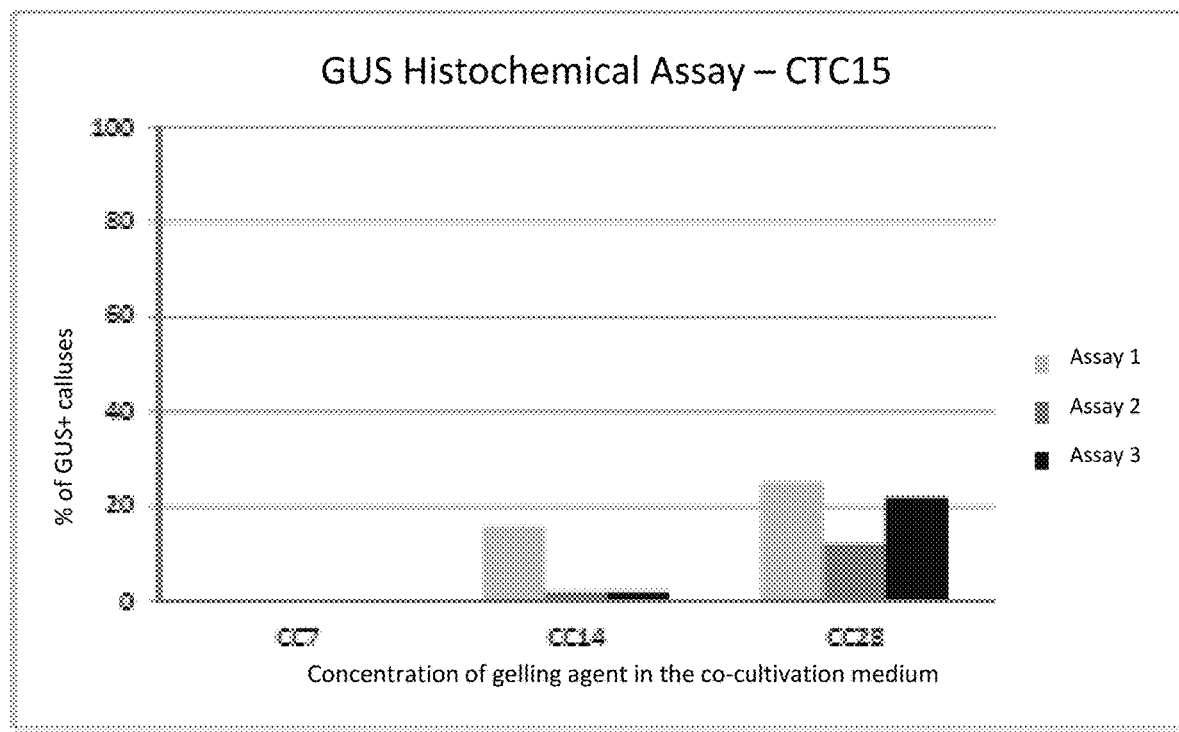
FIG. 3: Result of the histochemical evaluation of GUS for the CTC15 variety. Columns CC7: co-cultivation realized in 7 g/L of agargel; Columns CC14: co-cultivation realized in 14 g/L of agargel; Columns CC28: co-cultivation realized in 28 g/L of agargel.
Figure 4:
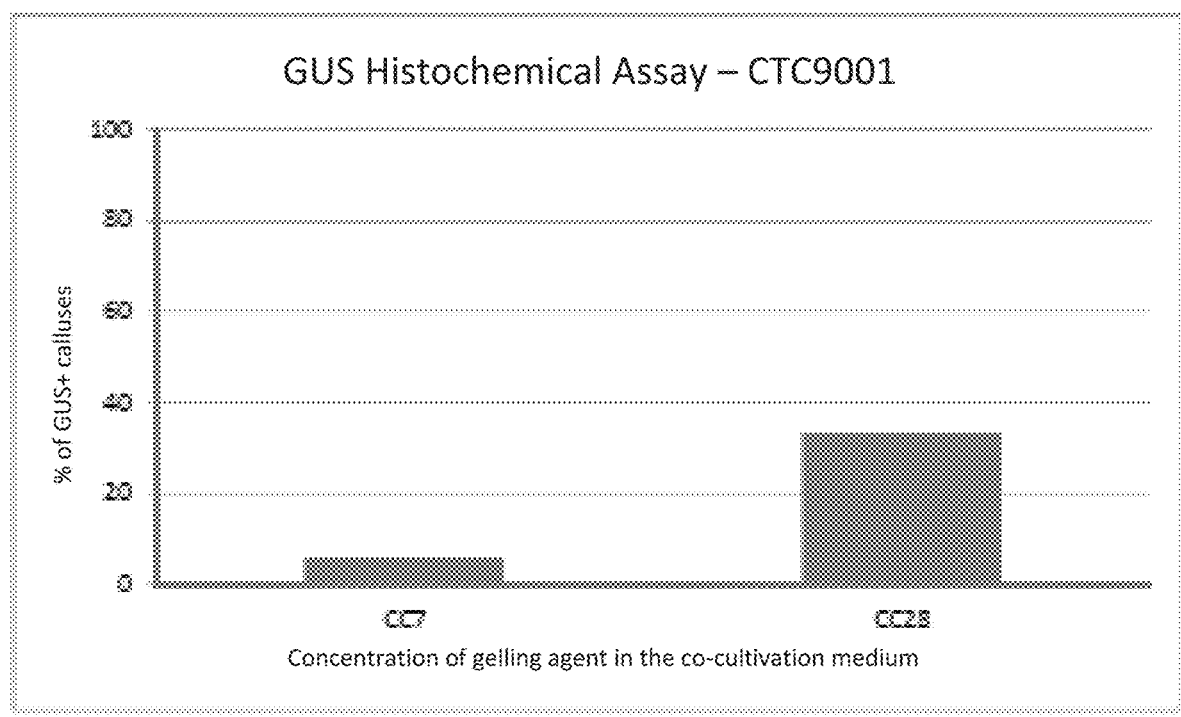
FIG. 4: Result of the histochemical evaluation of GUS for the 9001 variety. Columns CC7: co-cultivation realized in 7 g/L of agargel; Columns CC28: co-cultivation realized in 28 g/L of agargel.
Figure 5:
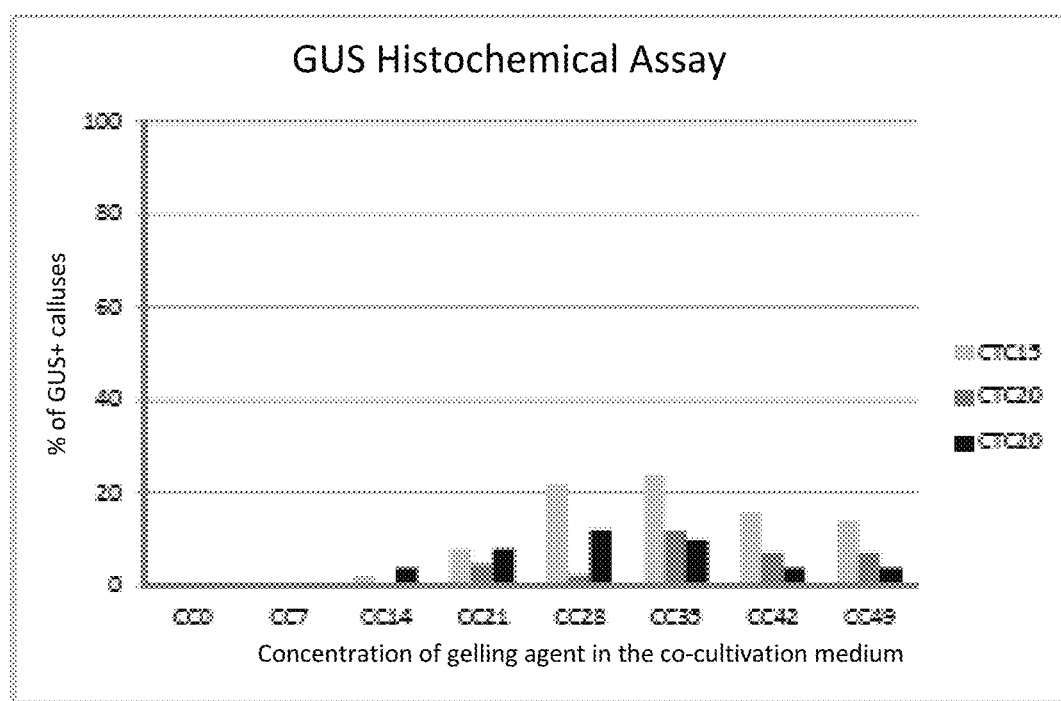
FIG. 5: Result of evaluation of different concentrations of agargel in the co-cultivation medium in the CTC15 and CTC20 varieties. Column CC0: co-cultivation realized in liquid medium; CC7: co-cultivation realized in 7 g/L of agargel; CC14: co-cultivation realized in 14 g/L of agargel; CC21: co-cultivation realized in 21 g/L of agargel; CC28: co-cultivation realized in 28 g/L of agargel; CC35: co-cultivation realized in 35 g/L of agargel; CC42: co-cultivation realized in 42 g/L of agargel; CC49: co-cultivation realized in 49 g/L of agargel.
Figure 6:
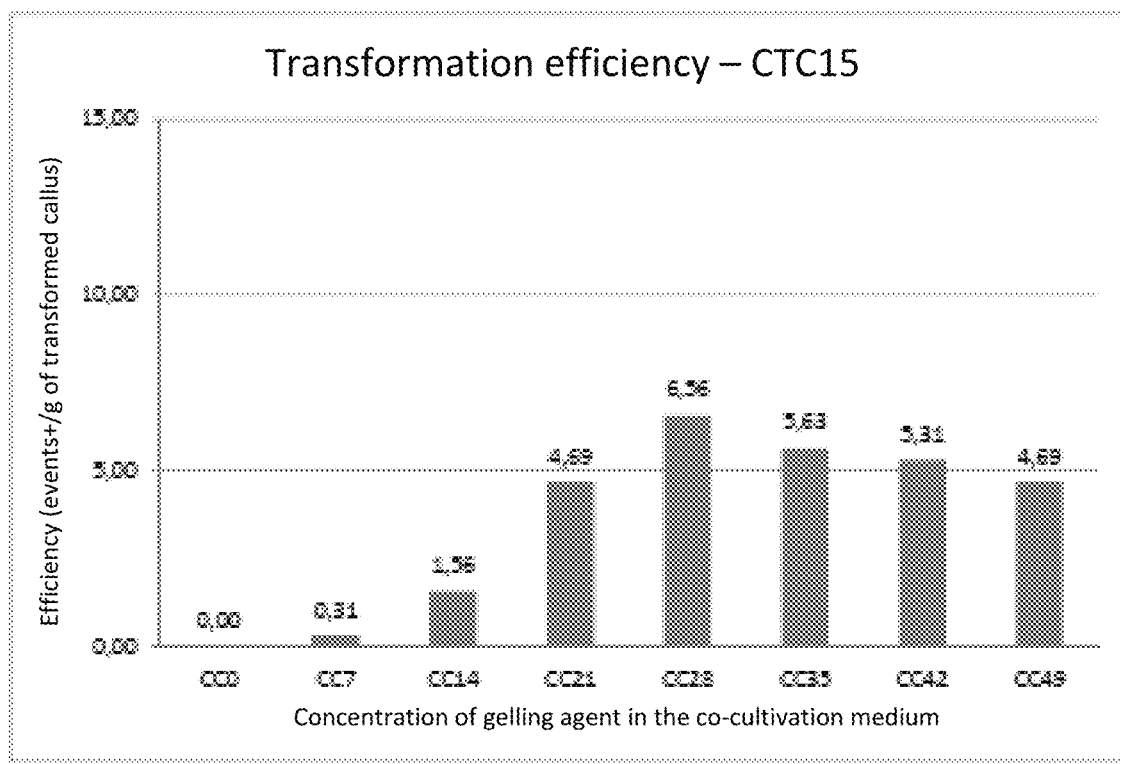
FIG. 6: Transformation efficiency result (number of positive events/g of transformed callus) of the CTC15 variety. Column CC0: co-cultivation realized in liquid medium; CC7: co-cultivation realized in 7 g/L of agargel; CC14: co-cultivation realized in 14 g/L of agargel; CC21: co-cultivation realized in 21 g/L of agargel; CC28: co-cultivation realized in 28 g/L of agargel; CC35: co-cultivation realized in 35 g/L of agargel; CC42: co-cultivation realized in 42 g/L of agargel; CC49: co-cultivation realized in 49 g/L of agargel.
Figure 7:
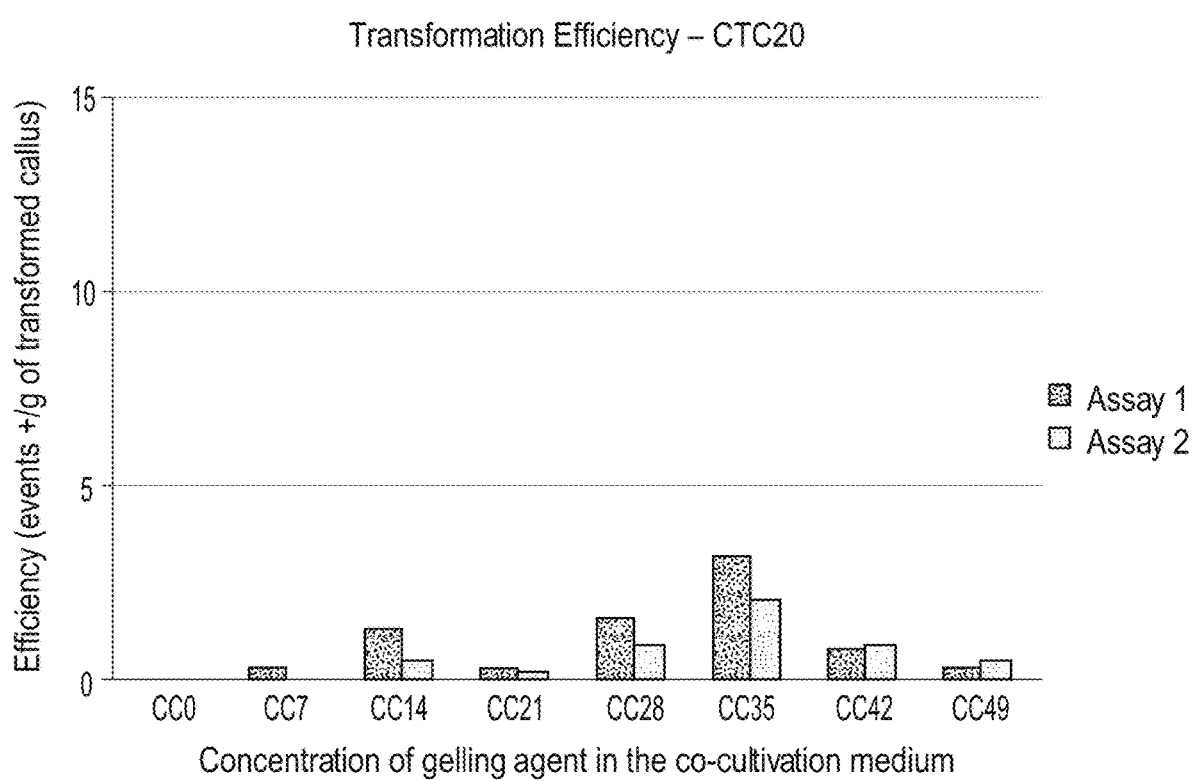
FIG. 7: Transformation efficiency result (number of positive events/g of transformed callus) of the CTC20 variety. Column CC0: co-cultivation realized in liquid medium; CC7: co-cultivation realized in 7 g/L of agargel; CC14: co-cultivation realized in 14 g/L of agargel; CC21: co-cultivation realized in 21 g/L of agargel; CC28: co-cultivation realized in 28 g/L of agargel; CC35: co-cultivation realized in 35 g/L of agargel; CC42: co-cultivation realized in 42 g/L of agargel; CC49: co-cultivation realized in 49 g/L of agargel.
Figure 8:
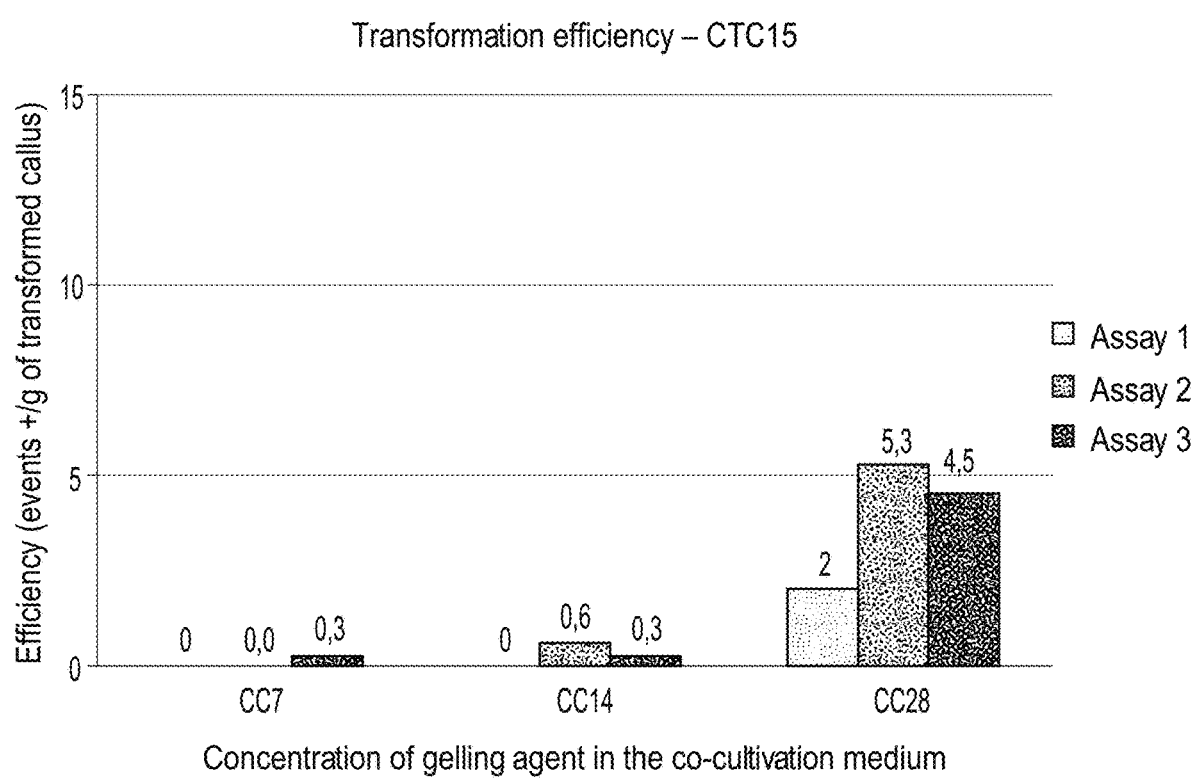
FIG. 8: Transformation efficiency result (number of positive events/g of transformed callus) of the CTC15 variety. Columns CC7: co-cultivation realized in 7 g/L of agargel; CC14: co-cultivation realized in 14 g/L of agargel; CC28: co-cultivation realized in 28 g/L of agargel.
Figure 9:
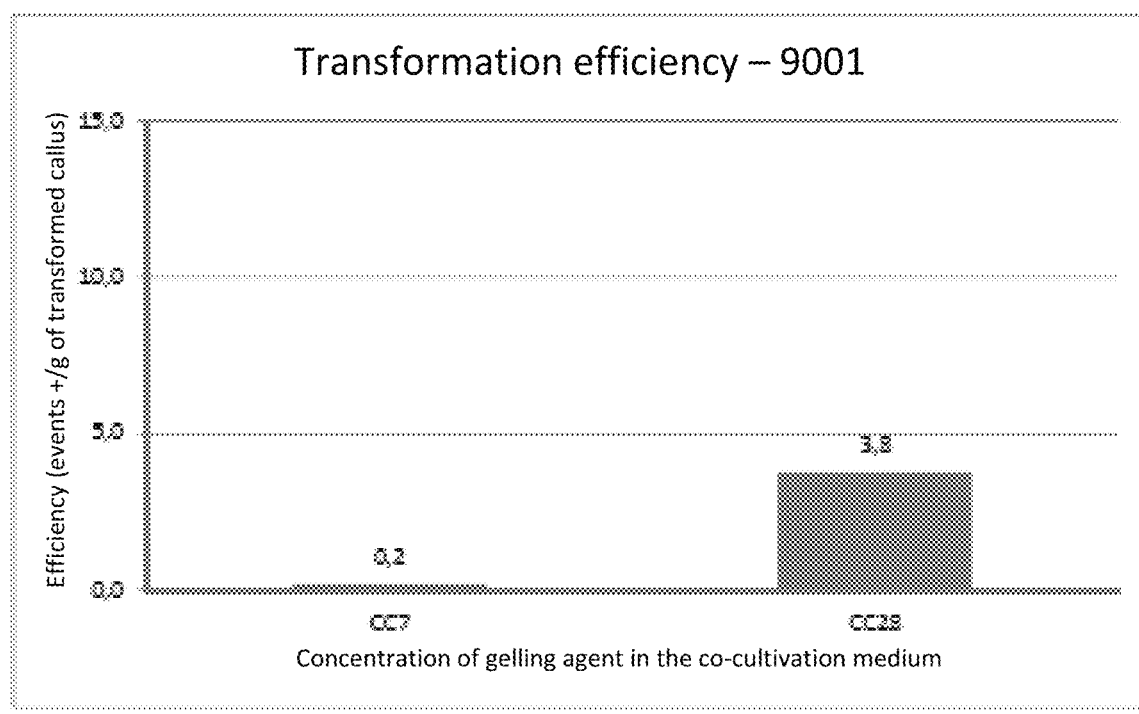
FIG. 9: Transformation efficiency result (number of positive events/g of transformed callus) of the 9001 variety. Columns CC7: co-cultivation realized in 7 g/L of agargel; CC28: co-cultivation realized in 28 g/L of agargel.

After co-cultivation, the calluses were transferred to the DT resting medium (Table 1) plus Timentim® bacteriostatic in a concentration of 200 mg/L in order to control undesirable growth of the *Agrobacterium* (FIG. 1). The rest period was 5-14 days at 26° C. in the dark. During this step, more precisely near five days of culture, a significant part of the calluses (around 50 units) was subjected to the GUS histochemical assay to detect the transient expression of the reporter gene and to monitor the process (FIGS. 3-5).

Example 4

Selection and Regeneration of Transgenic Plants

The calluses were transferred to the SGT selection medium (Table1), supplemented with 200 mg/L of Timentim®+50 mg/L of the geneticin selective agent when the selective gene nptII was used. The calluses remained in this condition for 21 days at 26° C. in the dark. Thereafter, the calluses were transferred to the RG1 regeneration medium, supplemented with 200 mg/L of Timentim®+30 mg/L of geneticin, and for a photoperiod of 16 hours at 4,000 lux.

Figures 2A, 2B:
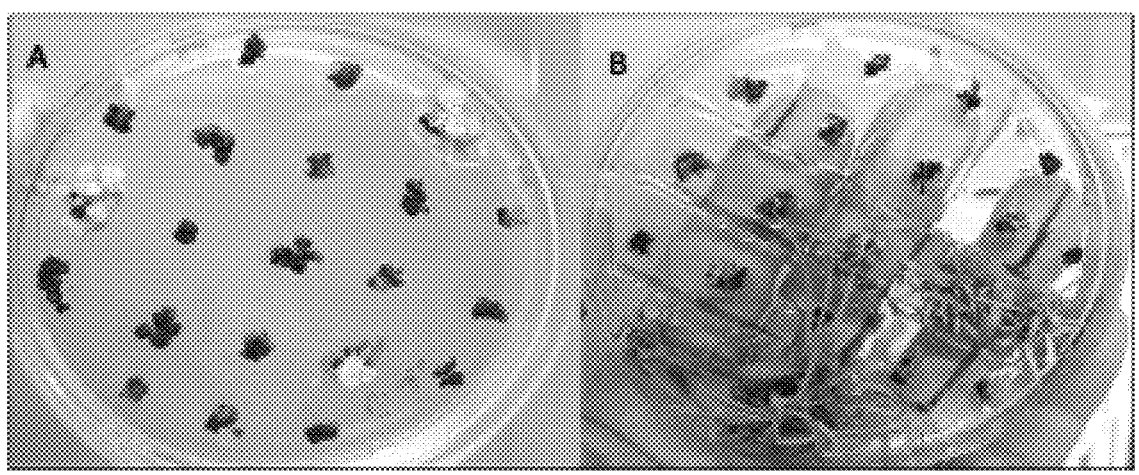
FIGS. 2A and 2B: Material subjected to the system of co-cultivation of present invention (28 g/L of agargel). A: thirty days in a regeneration medium 1 with selection of 50 mg/L of geneticin. B: plants being regenerated with event rastreability of sixty days in a medium with selection of 50 mg/L of geneticin.

After 30 days of light, the calluses showing the formation of seedlings without apparent stress to the selection by geneticin (FIG. 2) were transferred to the RG2 medium, supplemented with 200 mg/L of Timentim®+30 mg/L of geneticin. When the plants reached an average height of five centimeters, a leaf segment of about 20 mm was collected for quantitative real time PCR analysis. This methodology for determining the copy number is described as "Delta-Delta Ct" (Livak & Schmittgen. 2001. Analysis of relative gene expression data using Real-Time Quantitative PCR and the 2-ΔΔCT method. Methods 25: 402-408) which consists of a method using as calibrator (control) the average CT of three plants of a copy for the genes NPTII and GUS, confirmed by Southern Blot. The endogenous gene used as normalizer was polyubiquitin. The reactions were performed in multiplex format using a TaqMan probe for detecting the number of copies. The transformation efficiency was calculated as the ratio between the number of positive events for the amount (in grains) of calluses transformed in each experiment (FIGS. 6-9). Plant screening was maintained so as to prevent the subcloning of events. The set of assays carried out to obtain the results produced a total of 526 independent events analyzed by the qPCR technique.

Culture Media Used:

TABLE 1

| | Culture media | | | | | | |
|---|---|---|---|---|---|---|---|
| Reagents | SCIM Induction of calluses | CC Co-cultivation | DT Rest | SGT Selection | RG1 Regeneration 1 | RG2 Regeneration 2 | AGT Elongation |
| Salts MS (g/L) | 4.3 | 4.3 | 4.3 | 4.3 | 4.3 | 4.3 | 4.3 |
| Vitamins 1000x (mL/L) | 1 | 1 | 1 | 1 | 1 | 1 | 1 |
| Sucrose (g/L) | 25 | 25 | 25 | 25 | 25 | 25 | 25 |
| 2.4D (mg/L) | 3 | 3 | 3 | 3 | — | — | — |
| BAP (mg/L) | — | — | — | — | 1 | 0.1 | — |
| Casein (g/L) | 0.5 | — | 0.5 | 0.5 | — | — | — |
| Agar (g/L) | 7 | 7-50 | 7 | 7 | 7 | 7 | 7 |
| Timentin ® (mg/L) | — | — | 200 | 200 | 200 | 200 | 200 |
| Geneticin (mg/L) | — | — | — | 50 | 30 | 30 | 30 |
| Acetosyringone (μM) | — | 200 | — | — | — | — | — |
| pH | 5.7 | 5.4 | 5.7 | 5.7 | 5.7 | 5.7 | 5.7 |

Evidently the above examples are presented solely as illustrations, and the modification and variation thereof, obvious for those skilled in the art, are deemed to be included within the scope of the present invention, as defined in the accompanying claims.

The invention claimed is:

1. A method for transforming a sugarcane plant cell or plant tissue using *Agrobacterium* comprising:
    (a) contacting a plant cell or tissue with *Agrobacterium* containing at least a sequence of nucleotides of interest to be transferred to the plant cell or tissue;
    (b) co-cultivating the plant cell or tissue in a co-cultivation medium capable of supporting the growth of the plant cell or tissue and inhibiting the growth of *Agrobacterium*;
    (c) cultivating the cell or the tissue of step (b) in a medium comprising an agent capable of inhibiting the growth of *Agrobacterium*, and a selection agent to the transforming plant cell;
    (d) selecting at least a transforming cell comprising the sequence of interest,
    wherein in step (b), the co-cultivation medium comprises agar and gellan gum as gelling agent in concentrations from 21 g/L to 49 g/L,
wherein the gellan gum concentration is from 20 to 30% of total weight of the gelling agent.

2. The method according to claim 1 further comprising regenerating transgenic plants.
3. The method according to claim 1, wherein step (b) is performed for a period of about 1 to 30 days.
4. The method according to claim 1, wherein step (b) is performed for a period of 1 to 5 days.
5. The method according to claim 1, wherein the gelling agent is in a concentration of 28 g/L to 42 g/L.
6. The method according to claim 1, wherein the gellan gum concentration is from 20 to 25% of total weight of the gelling agent.
7. The method according to claim 1, wherein the gellan gum concentration is from 25 to 30% of total weight of the gelling agent.
8. The method according to claim 1, wherein the gellan gum concentration is from 23 to 27% of total weight of the gelling agent.
9. The method according to claim 1, wherein step (b) is conducted at 15° C. to 30° C.
10. The method according to claim 1, wherein step (b) is conducted at 20° C. to 25° C.
11. The method according to claim 1, wherein step (b) is conducted in the absence of light.
12. The method according to claim 1, wherein the plant cell or tissue is subjected to a rest period of about 1 to about 30 days after step (b) and before step (c).

* * * * *